(12) United States Patent
Chu et al.

(10) Patent No.: US 6,770,698 B1
(45) Date of Patent: Aug. 3, 2004

(54) POLYMER SOLUTION FOR SEPARATION OF CHARGED MACROMOLECULES BY ELECTROPHORESIS

(75) Inventors: Benjamin Chu, Setauket, NY (US); Liguo Song, Port Jefferson, NY (US); Dufei Fang, Painted Post, NY (US); Dehai Liang, Stony Brook, NY (US); Tianbo Liu, Stony Brook, NY (US)

(73) Assignee: The Research Foundation at State University of New York, Stony Brook, NY (US)

( * ) Notice: Subject to any disclaimer, the term of this patent is extended or adjusted under 35 U.S.C. 154(b) by 112 days.

(21) Appl. No.: 09/586,628

(22) Filed: Jun. 5, 2000

(51) Int. Cl.⁷ ............................................. C08L 51/00
(52) U.S. Cl. ...................... 524/458; 524/500; 524/501; 525/903
(58) Field of Search ........................ 524/458; 525/903

(56) References Cited

U.S. PATENT DOCUMENTS

| | | | |
|---|---|---|---|
| 4,985,128 A | | 1/1991 | Ebersole et al. |
| 5,069,766 A | | 12/1991 | Zhu et al. |
| 5,126,021 A | | 6/1992 | Grossman |
| 5,164,055 A | * | 11/1992 | Dubrow .................. 204/455 |
| 5,567,292 A | * | 10/1996 | Madabhushi et al. ....... 204/451 |
| 5,759,369 A | | 6/1998 | Menchen et al. |
| 5,885,432 A | * | 3/1999 | Hooper et al. ............. 204/469 |
| 5,916,426 A | | 6/1999 | Madabhushi et al. |

OTHER PUBLICATIONS

Liang, D., Zhou, S., Song, L., Zaitsev, V.S. and Chu, B., "Copolymers of Poly(N–isoprpylacrylamide) Densely Grafted with Poly(ethylene oxide) as High Performance Separation Matrix of DNA," *Macromolecules*, vol. 32(19), pp. 6326–6332 (1999).

Liang, D., Song, L., Zhou, S., Zaitsev, V.S., and Chu B., "Poly (N–isopropylacrylamide) –g–poly (ethyleneoxide) fro High Resolution and High Speed Separation of DNA by Capillary Electrophresis," *Electrophoresis*, vol. 20, pp. 2856–2863 (1999).

sSong. L., Fang, D., Kobos, R.K., Pace, S.J., and Chu, B. "Separation of Double–Stranded DNA Fragmetns in Plastic Capillary Electrophoresis Chips by Using $E_{99}P_{69}E_{99}$ as Separation Medium," *Electrophoresis*, vol. 20, pp. 2847–2855 (1999).

* cited by examiner

*Primary Examiner*—Kelechi C. Egwim
(74) *Attorney, Agent, or Firm*—Hoffman & Baron, LLP

(57) ABSTRACT

The present invention is a polymer solution for the efficient separation of charged macromolecules by electrophoresis that includes a plurality of polymers. These polymers are entangled to form an interpenetrating network with greater entanglement times than corresponding homopolymers of the same length. These polymers are different and do not phase separate when dissolved in solution. Preferred polymers are PAM and PVP or PDAM and PVP. The polymer solutions of the present invention provide at least a 500-base read length in one run for a single-stranded DNA separation.

9 Claims, 15 Drawing Sheets

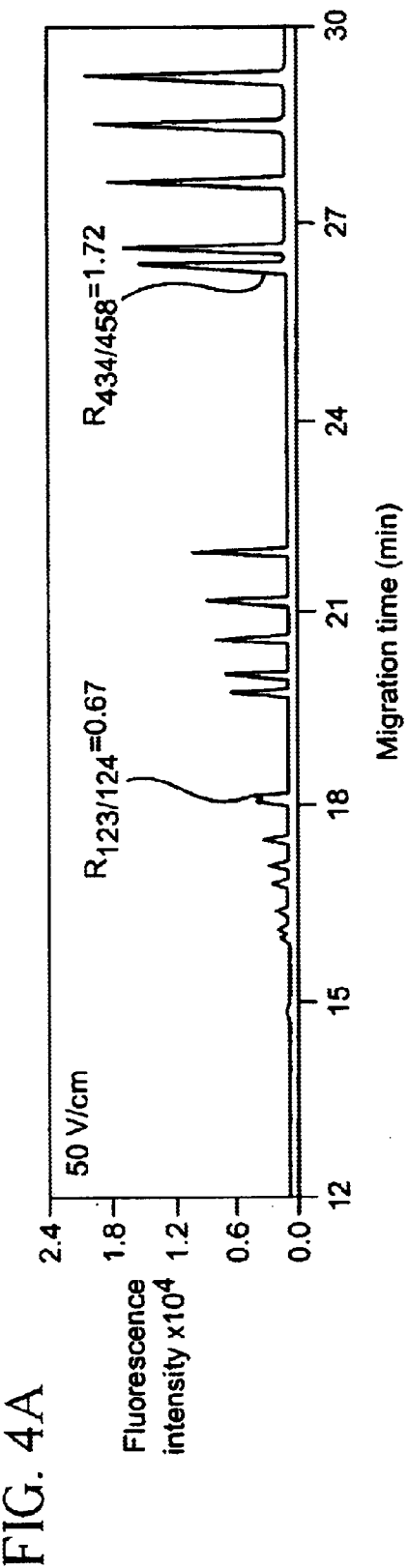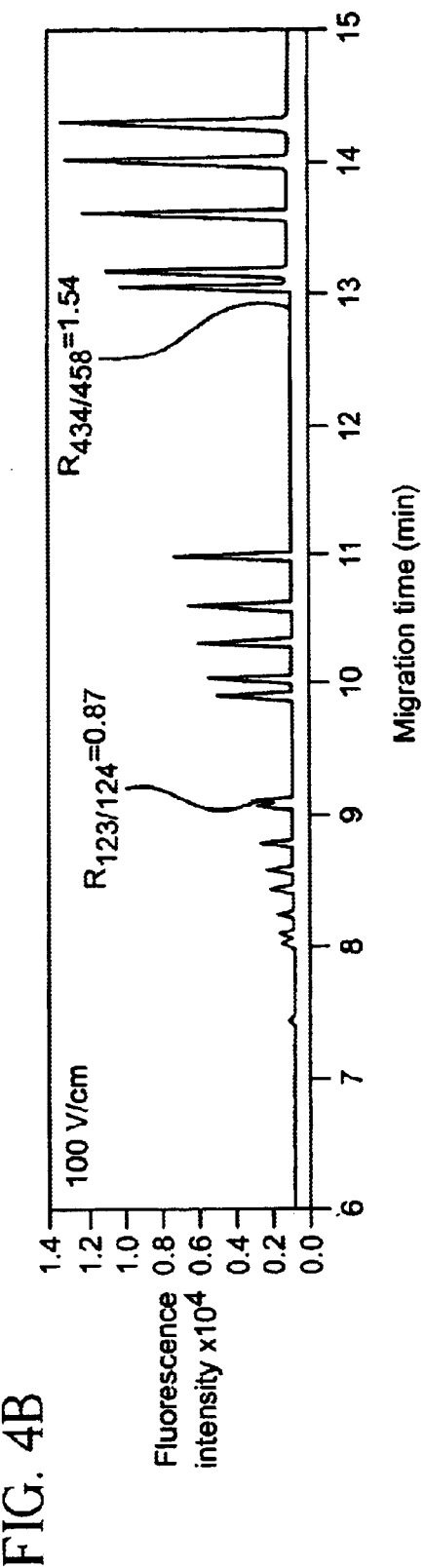
FIG. 4A
FIG. 4B

POLYMER SOLUTION FOR SEPARATION OF CHARGED MACROMOLECULES BY ELECTROPHORESIS

This invention was made with Government support under Grant No. 2R01HG0138604 awarded by the National Human Genome Research Institute. The Government has certain rights in the invention.

BACKGROUND OF INVENTION

The present invention relates generally to the art of separating charged molecular species, and, in particular, to separation media that are used for capillary electrophoresis.

Gel electrophoresis is one of the most widely used separation techniques in the biologically related sciences. Charged molecular species such as proteins, peptides, nucleic acids and oligonucleotides are separated by causing the species to migrate in a buffer medium under the influence of an applied electric field. The buffer medium normally is used in conjunction with a low to moderate concentration of an appropriate gelling agent, such as for example, agarose or cross-linked polyacrylamide, to promote the separation and to minimize the occurrence of mixing of the species being separated.

Until recently, electrophoretic separations were conducted in gel slabs or open gel beds that were typically fabricated of agarose or cross-linked polyacrylamide material. More recently, capillary electrophoresis ("CE") using a polymer gel or solution as a separation medium has been used for the separation of DNA. Capillary electrophoresis techniques combined with photometric detection methods have allowed the automation and rapid quantitative analysis of charged molecules. Furthermore, capillary electrophoresis can provide quantitative information about a sample using very small amounts of the sample, gel (or polymer solution) and buffer relative to traditional slab gel processes. Moreover, high-resolution separation of charged macromolecules having different effective charges have been achieved.

Typically, the capillary columns used in capillary gel electrophoresis are fabricated from fused silica tubing having diameters on the order of 25 $\mu$m to 200 $\mu$m and lengths from about 30 cm to about 200 cm. The column interior is filled with buffer and gel separation medium and electrophoretic techniques are used to separate charged molecular species.

Although the pore size of cross-linked polymer gels used for capillary electrophoresis can be controlled by the amount of monomers and cross-linked reagents, polymer gels have been found to be inconvenient as separation media for large scale DNA sequencing analysis due to the instability, irreproducibility and difficulty in controlling the polymerization process inside the capillary tubing.

The inability of many separation media to bind directly to the inner wall of the capillary tubes is a major problem for capillary electrophoresis methods because it creates an electro-osmotic flow when an electric field is applied during electrophoresis. Such migration results in an unsatisfactory separation of the constituent parts of the sample. Traditional methods aimed at preventing electro-osmosis include introducing a compound that binds to the inner surface of a capillary tube wall and that is compatible with the separation medium prior to injecting the separation medium into the tube. For example, U.S. Pat. No. 5,447,617 to Shieh describes covalently bonding polybutadiene to the inner surface of a capillary tube, introducing acrylamide monomers therein and co-polymerizing the acrylamide with the polybutadiene. Such precoating techniques, however, are time consuming, inconvenient and costly.

Another problem encountered in conventional capillary gel electrophoresis results from the use of polyacrylamide-based separation media. Such media are injected into the capillary tube in unpolymerized form. Polymerization of the polyacrylamide is then induced within the capillary tube by well known methods, such as ultraviolet radiation and chemical catalysts. Such methods are characterized by a lack of uniformity in the pore size distribution of the polymer network formed, and by incomplete polymerization.

The irreversible nature of the polymerized polyacrylamide gel also causes numerous problems when a polyacrylamide-based separation medium is used in capillary gel electrophoresis methods. Once the polyacrylamide is polymerized within a capillary electrophoresis tube, the polymerized gel cannot be easily removed from the capillary tube after electrophoresis.

Capillary electrophoresis ("CE") provides numerous advantages over conventional slab gel electrophoresis for DNA separation. The use of fused silica capillaries with inner diameters of less than 100 $\mu$m enables CE to operate at very high separation voltages and offers fast separation, high efficiency and increased resolution. In addition, rigid gels, which are normally used in slab gel electrophoresis because of their anti-convection ability, are not needed in capillary electrophoresis. Cross-linked polyacrylamide ("PAM") gels, which are widely used in conventional slab gel electrophoresis, were initially used in capillary electrophoresis. Despite successful results, i.e., 700 bases read lengths with resolution of 0.5 for DNA sequencing in about 230 minutes, PAM gels have encountered problems due to bubble formation, gel inhomogeneity, and short lifetime of the capillary.

Accordingly, attempts have been made to use nonpolymerized separation media for capillary electrophoresis. For example, U.S. Pat. No. 5,468,365 to Menchen et al. describes an electrophoresis medium having a matrix of aggregated copolymers dispersed in an aqueous in medium. The polymer matrix of the '365 patent is described as a dispersion of one substance (micelles) in another substance (water). In such a dispersion, the particles are formed by the association or aggregation of molecules having both hydrophilic and hydrophobic regions. The copolymers of the '365 patent form a polymer matrix having a relatively uniform mesh size which is believed to be related to the regular, i.e., substantially uniform spacing between adjacent hydrophobic polymer segments.

A number of different polymers have been used in CE methods to separate DNA fragments. Many of these polymers are modified polysaccharides, such as, agarose, methylcellulose ("MC"), hydroxypropyl-methyl-cellulose ("HPMC"), hydroxyethylcellulose ("HEC"), hydroxypropylcellulose ("HPC"), glucomannan, galactonmannan, and dextran. Some of them are synthesized polymers, such as, polyethylene glycol ("PEG"), polyethylene oxide ("PEO"), polyvinylpyrrolidone ("PVP"), polyvinylalcohol ("PVA"), polyacrylamide ("PAM"), poly-N-acryloyl-aminoethoxyethanol ("PAAEE"), polyacryloylaminopropanol ("PAAP"), poly-N,N-dimethylacrylamide ("PDMA"), polyacrylamide-co-allyl-$\beta$-D-glucopyranoside ("P(AM/AG)"), and poly-N-(acryloylaminoethoxyethyl-$\beta$-D-glucopyronoside ("PAEG"). Recently, polymers with viscosity dependent behavior have also been employed. One type of polymer was characterized by the collapse of molecules at high temperature, such as a copolymer of N,N-dimethylacrylamide and N,N-diethylacrylamide ("P(DMA/DEA)"), a copolymer of poly(N-isopropylacrylamide) ("PNIPAM") densely grafted with short poly(ethylene oxide) ("PEO") chains ("PNIPAM-g-PEO"), etc. Other polymers involved the formation of micelles, such as fluorocarbon end-capped polyethylene glycols, $E_{99}P_{69}E_{99}$ (with E being polyoxyethylene and P being polyoxyproplene), and n-dodecane-poly(ethylene oxide)-n-dodecane, etc. Each of these polymers has distinct advantages, but each also has inherent problems. For example, only several of them, such as HEC, PEO, PVP, PAM, PDMA, P(DMA/DEA), and fluorocarbon end-capped polyethylene glycols, have ever been used for DNA sequencing; and only HEC and high molecular weight PAM, PEO and PDMA have ever achieved a read length of greater than 500 bases.

Entangled polymer solutions, such as liquefied agarose, poly(acrylamide) ("PAM"), different kinds of cellulose, poly (ethylene oxide) ("PEO") or poly(dimethylacrylamide), have been widely used as a DNA separation medium in CE with some success. High molecular weight ($M_w$) PAM has achieved 1,000-base read length in one run for single-stranded DNA in run times of less than one hour. However, the PAM solution has two disadvantages: the injection is very difficult due to the very high viscosity, and the capillary inner wall has to be coated.

One base pair ("bp") resolution of double-stranded DNA has been achieved by using PEO mixtures without coating the capillary inner wall, but the solution viscosity is too high for easy injection. In addition, the capillary channels have to be pretreated with a low viscosity PEO solution before the high viscosity matrix is injected. PEO mixtures have also achieved 1,000 base read length with run times of about seven hours. Other polymers that have been used for single-stranded DNA are poly(dimethylacrylamide) which has achieved about a 600-base read length with run times of about two hours and HEC which has achieved up to about 500 bases with run times of about one hour. A number of other polymers have been used which have achieved read lengths of less than 500 bases.

Mixtures of the same polymer, such as PEO, HEC and PAM, with different molecular weights and mixtures of two modified polysaccharides, i.e., agarose and HEC, have been found to produce a better resolution for both small and large DNA fragments. However, a mixture of two polymers with totally different chemical structures has never been successfully used. Kim et al. (Kim, Y., Yeung, E. S., *J. Chromatogr. A.*, 1997, 781, 315–325) tried to use a mixture of PEO and HPC for DNA sequencing and found the separation to be very poor. The failure was attributed to the incompatibility of the two polymers The selection of the polymer used as the medium for DNA separation by capillary electrophoresis is very important because the polymer determines the migration behavior and the resolution of DNA fragments. An equally important issue in DNA separation by capillary electrophoresis is the coating of the inner wall of a fused silica capillary, which suppresses both electro-osmosis and the adsorption of DNA fragments onto the capillary inner wall. A coating protocol using PAM covalently attached to the capillary through a Si—O—Si bond has been widely used. Several modifications of this protocol using PVA, PAAEE, PAAP or PDMA have also been used. Because of the hydrolysis tendency of the Si—O—Si bond in an alkaline environment, PAM, PAAEE, PAAP or PDMA have even been covalently attached to the capillary by a Si—C bond. Some commercially available GC capillaries from J & W Scientific Inc. with coatings such as DB-1 (100% dimethylpolysiloxane), DB-17 (50% diphenyl 50% dimethylpolysiloxane) and DB-Wax (100% polyethyleneglycols) have also been used. Despite the wide use of covalently coated capillaries, the coating methods often increase their cost by requiring in situ synthesis and give rise to problems such as capillary fouling, coating inhomogeneity, and limited lifetime.

Speed is also important in DNA separation. In the past, pBR322/Hae III has been separated with PAM, PAAEE and PAAP in about one hour. By modifying PAM to have less viscosity, shorter separation times of about tens of minutes have been achieved. With cellulose derivatives and PEO, the separation time is about twenty to thirty minutes. A 13-min separation of pBR322/Hae III has been achieved using the present invention with a separation medium of PNIPAM-g-PEO. Muller et al. has achieved an ultra-fast separation of pBR322/Hae III in 30 seconds with 1% MC. To achieve such a separation, a shorter effective separation length of 3 cm, a higher applied electric field strength of 800 V/cm and a narrower plug electrokinetic injection of 100 ms at 600 V/cm with a fast ramp power supply were employed. However, the separation of 434, 458 and 504 bp was hardly visible. And the partly separated 123/124 bp was a result of the structurally dependent migration at high electric field strengths rather than a result of single base pair resolution.

PAM gels have become less popular due to bubble formation, gel inhomogeneity, and short lifetime of the capillary. These problems have been eliminated in the present invention through the use of non-crosslinked polymer solutions. These polymer solutions can be replaced after each electrophoresis run if necessary, which makes CE particularly well suited for automation.

Accordingly, it would be desirable to provide a new separation medium for capillary electrophoresis methods, which has alleviated the bubble formation problem and reduced the inhomogeneity of the separation medium. It would also be desirable to provide a separation medium that has increased capillary lifetime and does not require coating of the interior surface of a capillary tube. In particular, it would be desirable to provide a separation medium that provides high resolution and is easy to apply and remove from various apparatus.

SUMMARY OF THE INVENTION

The present invention is a polymer solution for the efficient separation of charged macromolecules by electrophoresis that includes a plurality of polymers. These polymers are different, do not phase separate when dissolved in solution and are entangled to form an interpenetrating network. In some embodiments, these polymers are neutral and water-soluble. Preferred polymer solutions of the present invention provide at least a 500-base read length in one run for a single-stranded DNA separation.

At least one of the polymers in the polymer solution is PAM, N-substituted PAM, N,N-disubstituted PAM, modified polysaccharides, PEO, PVP, PVA, PEG, or a random, a graft or a block copolymer based on the backbone monomer segments thereof. The nitrogen substitutes are $C_1$ to $C_3$ alkyl, hydroxyl-substituted $C_1$ to $C_3$ alkyl or methoxy-substituted $C_1$ to $C_3$ alkyl. The random, graft or block copolymer can be EPE-type Pluronics, P(DMA/DEA), PNIPAM-g-PEO or P(AM/AG). The polysaccharides can be liquified agrose, MC, HEC, HPMC, HPC, glucomannan, galactonmannan and dextran.

In a preferred embodiment, at least one of the polymers in the polymer solution is a silica-absorbing polymer that suppresses electrophoendoosmotic flow and charged macromolecule-silica interactions. The silica-absorbing polymer can be PVP, PEO, EPE-type Pluronics, N-substituted PAM or N,N-disubstituted PAM. The nitrogen substitutes can be $C_1$ to $C_3$ alkyl, hydroxyl-substituted $C_1$ to $C_3$ alkyl, or methoxy-substituted $C_1$ to $C_3$ alkyl.

The interpenetrating network polymer solution has a more expanded structural formation than the entanglement structure of a corresponding homopolymer solution and it has a larger effective size than that of a corresponding homopolymer solution. This represents an effective entanglement network greater than that of the corresponding homopolymers. The interpenetrating network can be prepared by synthesizing a first polymer in a matrix of a second polymer solution or by dissolving together the two polymers in a solvent.

Another embodiment of the present invention is a polymer solution for the efficient separation of charged molecules by electrophoresis that can provide at least a 500-base read length in one run for a single-stranded DNA separation. The polymer solution includes a plurality of stretched polymer chains that have polymer chain entanglement times greater than the corresponding linear homopolymer solution. The polymer chains include the same polymer or a plurality of different polymers. These polymer chains can entangle to form an interpenetrating network in solution. Preferred polymers are PAM and PVP or PDAM and PVP.

The polymer chains can include a random copolymer made up of a monomer taken from PAM, N-substituted PAM, N,N-disubstituted PAM, modified polysaccharides, PEO, PVP, PVA or PEG. The random copolymer can also include a silica-absorbing segment taken from PVP, PEO, EPE-type Pluronics, N-substituted PAM or N,N-disubstituted PAM, wherein nitrogen substitutes can be $C_1$ to $C_3$ alkyl, hydroxyl-substituted $C_1$ to $C_3$ alkyl, or methoxy-substituted $C_1$ to $C_3$ alkyl. In a preferred embodiment, the random copolymer is made up of AM and DMA.

The polymer chains can include a graft copolymer that includes a monomer taken from PAM, N-substituted PAM, N,N-disubstituted PAM, modified polysaccharides, PEO, PVP, PVA or PEG. The graft copolymer can also include a silica-absorbing segment taken from PVP, PEO, EPE-type Pluronics, N-substituted PAM or N,N-disubstituted PAM, wherein nitrogen substitutes can be $C_1$ to $C_3$ alkyl, hydroxyl-substituted $C_1$ to $C_3$ alkyl, or methoxy-substituted $C_1$ to $C_3$ alkyl. In a preferred embodiment, the graft copolymer includes PNIPAM-g-PEO.

The polymer chains can include a very weakly cross-linked microgel that includes a monomer taken from PAM, N-substituted PAM, N,N-disubstituted PAM, modified polysaccharides, PEO, PVP, PVA or PEG. The very weakly cross-linked microgel can also include a silica-absorbing segment taken from PVP, PEO, EPE-type Pluronics, N-substituted PAM or N,N-disubstituted PAM, wherein nitrogen substitutes can be $C_1$ to $C_3$ alkyl, hydroxyl-substituted $C_1$ to $C_3$ alkyl, or methoxy-substituted $C_1$ to $C_3$ alkyl. In a preferred embodiment, the very weakly cross-linked microgel includes PAM and a hydrophilic cross-linker, preferably PEO diacrylate.

The polymer solution of the present invention satisfies the need for improved DNA separation media that can also be used to dynamically coat the inner capillary wall. In addition, the separation media of the present invention are easier to use because they are not strongly cross-linked and they provide improved resolution and faster run times.

BRIEF DESCRIPTION OF THE FIGURES

Other objects and many attendant features of this invention will be readily appreciated as the invention becomes better understood by reference to the following detailed description when considered in connection with the accompanying drawings wherein:

FIGS. 4A–4D show the test results for a separation of pBR 322/Hae III DNA by CE in interpenetrating networks of PAM and PVP using different electric field strengths.

Figure 1A:
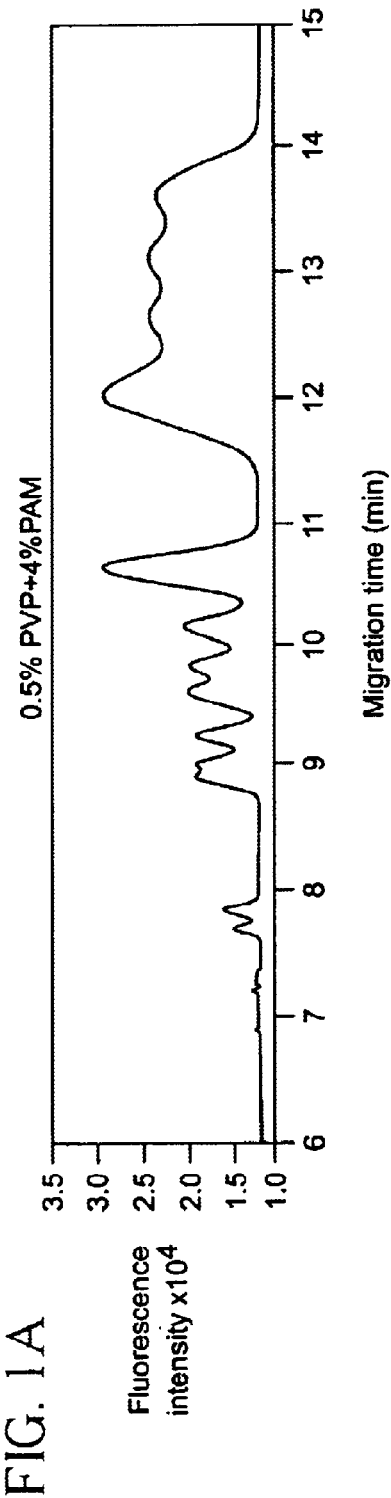
FIGS. 1A–1D show the test results for a separation of pBR 322/Hae III DNA by CE in interpenetrating networks of a fixed amount of PAM and varying amounts of PVP.
Figure 1B:
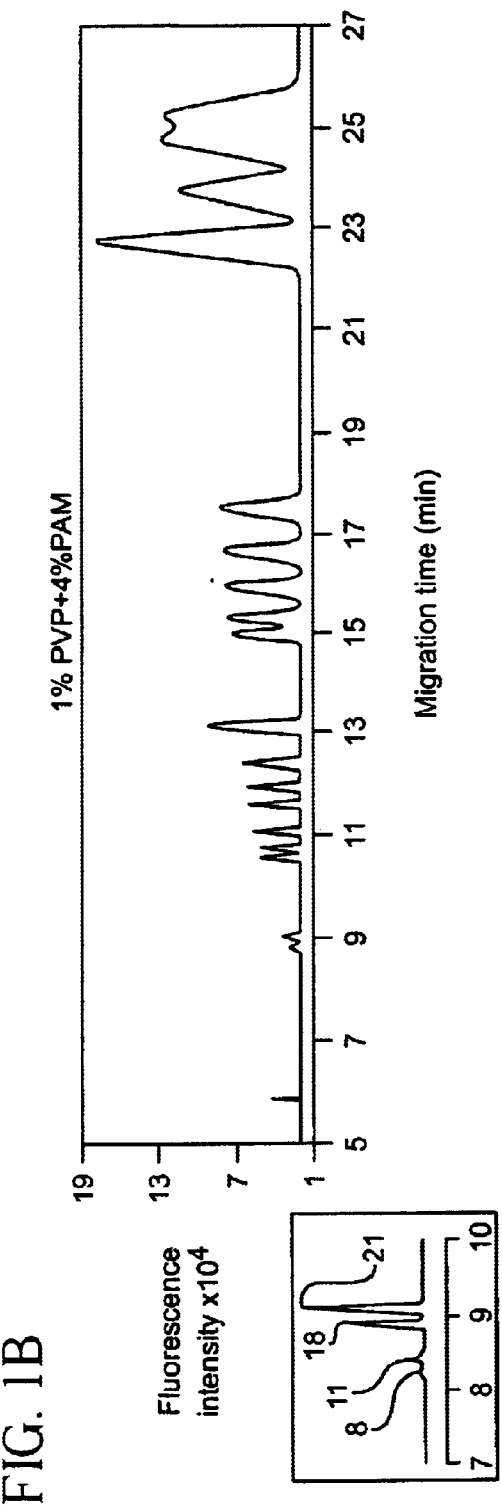
Figure 1C:
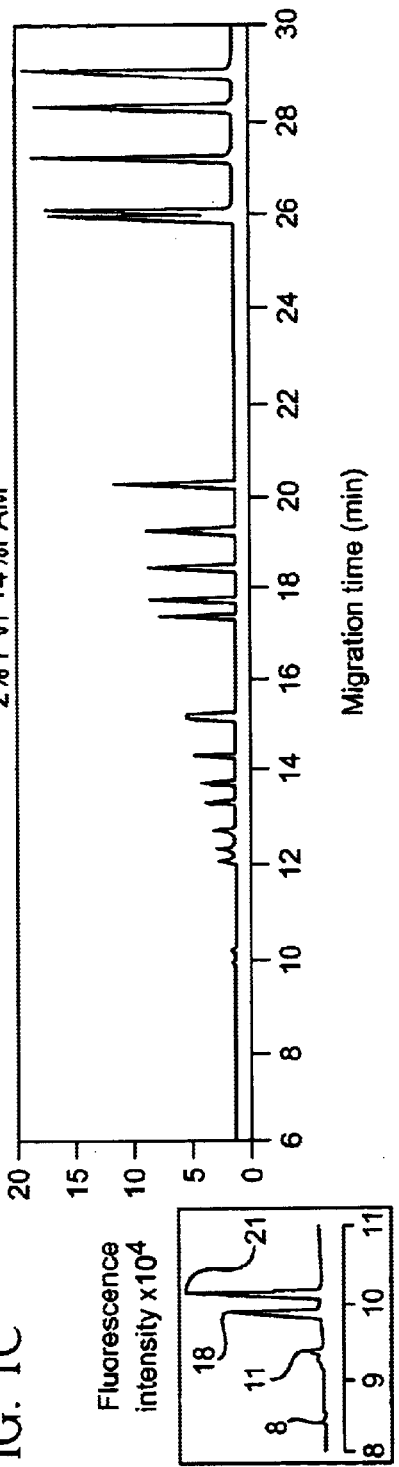
Figure 1D:
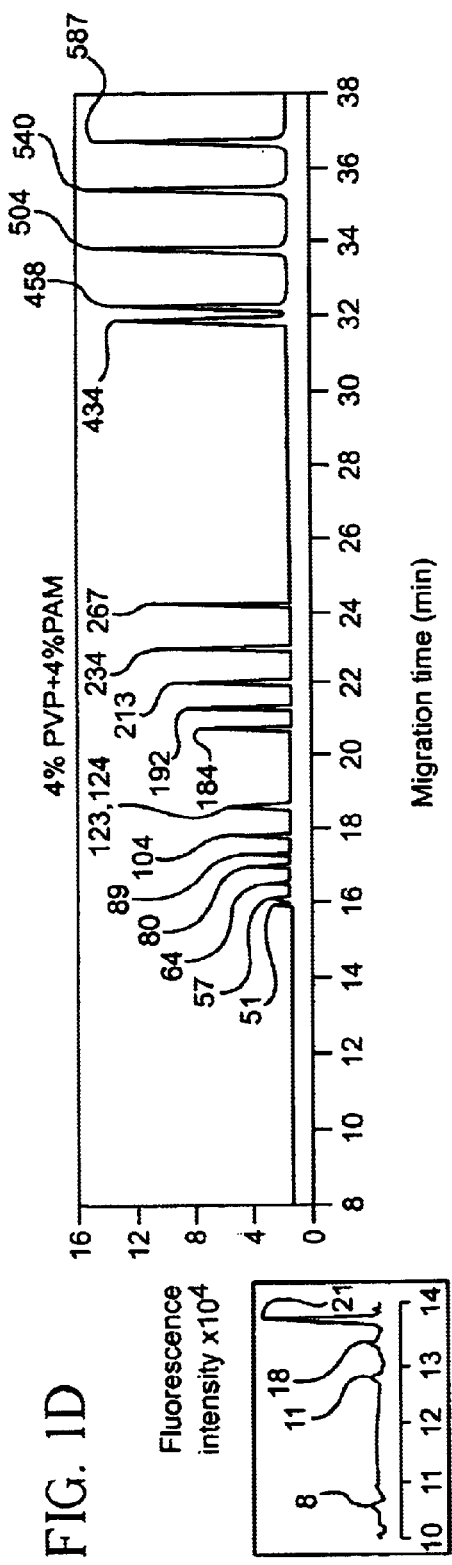

The percentages shown in the drawings are weight/volume percentages (w/v %).

DETAILED DESCRIPTION OF THE INVENTION

The present invention is a method of preparing a capillary electrophoresis separation medium that includes one or more polymers. For example, the separation medium is made up of two polymers, wherein the first and the second polymers are different. The separation medium can exist as interpenetrating networks, random copolymers and/or graft copolymers. One method of forming the interpenetrating network is by synthesizing the first polymer in the presence of the second polymer. The forced entanglement of two or more polymers can also form the interpenetrating network.

The separation medium that is made up of two (or more) polymers can be chosen from a broad range of water-soluble neutral polymers, such as agrose, MC, HPMC, HEC, HPC, PEG, PEO, PVP, PVA, PAM, PAAEE, PAAP, PDMA, P(AM/AG), PAEG, P(DMA/DEA), PNIPAM, PNIPAM-g-PEO, the Pluronics and fluorocarbon end-capped polyethylene glycols, etc. At least one of the two (or more) polymers should have dynamic surface coating ability.

In one embodiment, the first polymer is a (modified) polyacrylamide, preferably poly(acrylamide) (PAM). In other embodiments, the first polymer is a modified polysaccharide, such as hydroxyethylcellulose (HEC), a copolymer N,N-dimethylacrylamide and N,N-diethylacrylamide P(DMA/DEA) or a fluorocarbon end-capped polyethylene glycol.

The second polymer is preferably poly(vinylpyrrolidone), poly-N,N-dimethylacrylamide (PDMA) or polyethylene oxide (PEO). Other polymers which are reactive with the SiOH group of a fused silica compound can also be used. In a preferred embodiment, the first polymer is poly(acrylamide) and the second polymer is poly(vinylpyrrolidone) or poly-N,N-dimethylacrylamide (PDMA). The separation methods of the present invention preferably achieve at least a 500-base read length in one run for single-stranded DNA fragments.

In addition, the present invention includes a method of preparing a capillary electrophoresis separation medium having a selected mesh size. The method includes selecting a desired mesh size for the separation medium and then determining the ratio of the amount of a first polymer to the amount of a second polymer that is required to provide this mesh size, wherein the first and the second polymers are different and do not exhibit phase separation when dissolved together in a solvent. One method is to synthesize the first polymer in a solution of the second polymer to form a separation medium that has interpenetrating networks of the first and second polymers.

The first polymer and the second polymer are the same as the polymers discussed above and the separation medium formed from these polymers achieves a read length of at least 500 bases in one run for single-stranded DNA fragments. For example, the weight ratio of the first polymer (PAM) to the second polymer (PVP) is from about 1:12 to about 16:1, preferably from about 1:2 to about 2:1 and most preferably about 1:2.

The present invention is also a capillary electrophoresis separation system made up of entangled polymer chains that provide a mesh size effective to achieve a single-base resolution and at least 500 bases in one run for single-stranded DNA fragments. The polymer entanglement in the interpenetrating network includes a first polymer and a second polymer which are structured so that the polymer entanglement has a lower weight to volume ratio than the combined weight to volume ratios of the first polymer and the second polymer. In one embodiment, the first polymer is a (modified) polyacrylamide and the second polymer is reactive with the SiOH group of a fused silica compound.

In a preferred embodiment, the polymer entanglement used in the capillary electrophoresis separation system is an interpenetrating network of two or more polymers. Each polymer can be a linear homopolymer, a graft copolymer, a random copolymer, a weakly cross-linked microgel or a combination of two or more thereof The polymer entanglement can include an interpenetrating network that contains a synthesis of the first polymer and second polymer, wherein the first and said second polymers are different and do not phase separate when dissolved together in a solvent. The graft copolymer is made up of short chain polymers having a first monomer grafted to a backbone polymer chain that contains a second monomer, wherein the first and second monomers are different. The random copolymer is a polymer chain having both a first monomer and a second monomer, wherein segments (or regions) of the monomers tend to repel each other.

The separation media of the present invention are formed by combining two or more different neutral, hydrophilic, stable materials with at least one having surface active properties in an interpenetrating network in order to take advantage of the properties of each of the polymers. These interpenetrating networks have an appropriate mesh size and sufficient surface activity to suppress electro-osmosis and DNA adsorption on the substrate containing the separation medium. Highly entangled interpenetrating networks require a minimal amount of polymers in solution while achieving a large dynamic range for separation of macromolecular fragments. Consequently, charged macromolecular separation can occur in a relatively short run time. In order to attain structure for rapid separation, the combined polymer chains are more extended or "stretched" when compared to corresponding homopolymer chains in the same buffer solution. Thus, the separation medium of the present invention requires a smaller amount of polymer to produce a network of the same effective mesh size. The present invention also increases the polymer chain entanglement times in order to simulate a chemically cross-linked gel. This allows the separation medium of the present invention to separate larger size fragments.

The present invention uses the concept of interpenetrating networks, to combine two different polymer chains in such a manner that the chains are stretched beyond their normal conformation. Different-types of polymer chains tend to resist combining with each other. This is caused by the incompatibility of different polymer chains. The incompatibility forces the different polymer chains to move away from each other. It has been found that the exertion of these forces results in the polymer chains being extended or "stretched." The "stretched" polymer chain conformations have the same molecular weight as they did prior to being mixed to form the interpenetrating network. It has been found that these "stretched" polymer chains provide a more effective separation medium.

Extended polymer chains and increased polymer chain entanglement times can also be accomplished by grafting a small amount of short-chain polymer having a different kind of monomer to the backbone of a main chain polymer. This procedure is described in two articles titled: "*Copolymers of Poly(N-isopropylacrylamide) Densely Grafted with Poly(ethylene oxide) as High-Performance Separation Matrix of DNA*," Liang, D., Zhou, S., Song, L., Zaitsev, V., and Chu, B., *Macromolecules*, Vol. 32, No. 19, pp. 6326–6332 (1999) and "*Poly(N-isopropylacrylamide)-g-poly(ethyleneoxide) for high resolution and high speed separation of DNA by capillary electrophoresis*," Liang, D., Song, L., Zhou, S., Zaitsev, V., and Chu, B., *Electrophoresis*, Vol. 20, pp. 2856–2863 (1999). Both of these references are incorporated herein in their entirety.

Grafting short chains of a different kind to the polymer backbone is a tedious procedure because each change in the length of the side chain and the density of the side chain requires a complete synthetic step and characterization. However, polymer chains produced by this all grafting method have increased polymer chain entanglement times, which provide a better separation medium for capillary electrophoresis.

In another embodiment, the separation medium can be extended by using random copolymers that include an appropriate ratio of two different monomers in the same polymer backbone chain. The various short "blocks" of different monomer segments in the backbone tend to repel each other, which results in the overall random copolymer chains being more extended in some regions. In addition, the different polymer segments increase the intrachain entanglement points in other regions of the polymer chain backbone. The local aggregation behavior causes the polymer chains to stay together for longer periods of time, further enhancing the effectiveness of the separation medium.

The effectiveness of the separation medium can also be improved by selecting one monomer segment, which is more surface active than the other monomer segment due to a difference in hydrophobicity. This provides a more effective separation medium than a backbone polymer having monomer segments with similar hydrophobicity. An example of such a separation medium is a random copolymer of acrylamide and dimethyl acrylamide, which has shown a significant improvement in electrophoresis data when tested.

Chemical cross-linking is one method of increasing the entanglement times of polymer chains and such cross-linked polymers are particularly well suited for the separation of large size DNA fragments. Unfortunately, chemically cross-linked gels are not easy to handle and create several problems when used in capillary electrophoresis. The present invention takes advantage of the benefits that cross-linking provides by using a very weakly cross-linked microgel. The weakly cross-linked microgels of the present invention have some permanent cross-linking points and increase the effective polymer molecular weight of the separation medium, while avoiding the problems associated with polymers that have been extensively cross-linked. These very weakly cross-linked microgels improve the effectiveness of the separation media of the present invention. The very weakly cross-linked microgels can make up either one or both of the polymers used in forming the interpenetrating network of the separation medium.

The separation media of the present invention can use interpenetrating networks, graft copolymers, random copolymers, weakly cross-linked microgels or a combination of two or more of these methods to provide increased polymer entanglements without an increase in molecular weight. The increase in entanglement times provides better separation and the lower polymer concentration of the medium allows faster run times. These characteristics are particularly useful in the field of capillary electrophoresis. Using the separation medium of the present invention, a read length of over 1000 bases in a sequencing buffer has been achieved in a short run time. The present invention combines the advantages of two dissimilar polymers, such as PAM and PVP, to provide an improved separation medium.

Two important issues in DNA separation by capillary electrophoresis are the selection of the separation medium and coating the inner wall of a fused silica capillary. The selection of the separation medium determines the migration behavior and the resolution of DNA fragments. The coating of the inner capillary wall insures the accuracy of the separation measurement by suppressing both electro-osmosis and the adsorption of DNA fragments. The present invention solves the problem of coating the inner capillary wall by using an alternative dynamic coating protocol. The dynamic coating protocol uses the molecular interaction (mainly hydrogen bond) between the Si—OH group of the capillary inner wall and the separation medium. Polymers, such as PEO, $E_{99}P_{69}E_{99}$, PDMA and PVP, have been found to provide the strongest interactions.

As a separation medium, PAM and PVP each have distinct advantages and drawbacks. Of all the polymers currently in use, PAM gives one of the highest resolutions for both double stranded and single stranded DNA fragments. The major problem encountered when using PAM as a separation medium in capillary electrophoresis is that PAM cannot dynamically coat the capillary inner wall. When compared with PAM, PVP produces significantly poorer results when used as a separation medium. However, PVP is much less viscous (a 4.5% weight/volume (w/v) PVP with a molecular weight of 1 MDa has a viscosity of 27 cP at 30° C.) than PAM and dynamically coats the interior walls of the capillary when used as a separation medium for capillary electrophoresis.

The interpenetrating networks of the present invention are formed from two or more different polymers, which do not phase separate when they are dissolved together in a solvent. Instead, the essentially immiscible polymer chains have to be effectively entangled to form an interpenetrating network in solution. For example, PVP and PAM were formed into a network by synthesizing PAM in a PVP solution matrix. The present invention combines different polymers to take advantage of the desirable characteristics of each of the polymers. For example, PAM (a good separation medium) is combined with PVP (a separation medium which does not require precoating of the inner capillary wall) to provide an interpenetrating network of PVP and PAM which can dynamically coat the inner wall of a fused silica capillary and becomes a better separation medium than PAM.

The present invention uses a mixture of two polymers with different chemical structures to form interpenetrating networks that provide an improved separation medium and dynamically coat the inner capillary walls. The separation media take advantage of the characteristics of the different polymer structures to provide increased resolution and faster run times. Laser light scattering studies showed the formation of interpenetrating networks. The presence of interpenetrating networks is responsible for the better separation.

PAM gels have encountered problems due to bubble formation, gel inhomogeneity, and short lifetime of the capillary. These problems have been eliminated in the present invention through the use of non-crosslinked polymer solutions. The interpenetrating networks of the present invention can be easily removed from the capillary because the polymers are not chemically bound together by cross-inks. Thus, these polymer solutions can be replaced after each electrophoresis run if necessary, which makes the separation media of the present invention well suited for automated capillary electrophoresis.

For a given polymer, the optimization of separation conditions for capillary electrophoresis in DNA sequencing analysis depends on three primary factors: the polymer concentration, the sample injection amount and the electric field strength. The concentration of the polymer in the separation medium affects the resolution, the run time and the read length. Higher concentrations provide higher resolution, while lower concentrations provide lower viscosity, faster separation and longer read length. The optimum concentration would have sufficient resolution at the lowest possible concentration. The amount of sample injected affects the resolution as well as the signal to noise ratio. For optimum results, the injection amount should be kept to a minimum in order to provide high resolution and a sufficiently high signal to noise ratio. The electrical field strength is moderately high, about 150 V/cm. A higher electric field strength provides faster separation and higher resolution for smaller fragments. However, if the electric field strength is too high, larger fragments will have lower resolution and the read length will be shorter.

EXAMPLES

Capillary Electrophoresis Procedures

For the tests described in the examples, a 12-cm long fused silica capillary (Polymicro Technologies, Phoenix, Ariz.) with ID/OD of 100 or 50/365 µm was flushed with 1 M HCl for about 10 minutes. A detection window was opened at 2 cm from the cathodic end of the capillary by stripping off the polyimide coating with a razor blade. A gas tight syringe was then used to fill the capillary with the separation medium. Before each electrophoresis run, the capillary column was conditioned under an electric field strength of 200 V/cm until the current became stable (generally about 10 min). During this period, ethidium bromide migrated into the capillary from the buffer. The DNA sample was then electrokinetically injected into the capillary at an electric field strength of 50 V/cm for 3 seconds. The running electric field strength was generally 100 V/cm, although some tests were carried out at different field strengths.

Static light scattering (SLS) and dynamic light scattering (DLS) measurements were used to characterize the polymer systems in aqueous solution. The measurements were made using a standard laboratory-built light scattering spectrometer, which was capable of both SLS and DLS measurements over an angular range of 15–140°. The spectrometer was equipped with a 200 mW diode-pumped solid-state (DPSS) laser (Coherent Radiation Model 532) operating at 532 nm and a Brookhaven Instruments (BI 9000) correlator. The sample chamber included a thermostat, which controlled the temperature to within ±0.02° C. The intensity-intensity time correlation functions were analyzed by the constrained regularization method developed by S. W. Provencher (see Provencher, S. W., "Makromol. Chem." 1979, 180, 201, Comput. Phys. Commun., 1982, 27, 213, 229), known as the CONTIN method. From the SLS measurements, the weight-average molecular weight ($M_w$) of the macromolecules was determined, while DLS measurements provided information on particle size (in terms of hydrodynamic radius, $R_h$) and particle size distribution.

The resolution (R) for the test results was calculated using the following equation:

$$R=[2(t_2-t_1)/(w_1+w_2)] \quad (1)$$

where $t_1$, $t_2$, are the migration times and $w_1$ and $w_2$ are the temporal peak widths of the DNA fragments.

The DNA Sample

The separation of pBR322/Hae III is widely used for testing the sieving ability of separation media because pBR322/Hae III has 22 DNA fragments in the range of 8 bp to 587 bp. This interval covers most polymerase chain reaction (PCR)-amplified DNA chains produced for analysis of genetic diseases. In addition, the base pair intervals of adjacent fragments in this sample are small enough to test the sieving ability of separation media. Prior to the present invention, good separation of the 123 bp from 124 bp had not been achieved without using intercalating dyes in the buffer. In the presence of an intercalating dye in the running buffer, some polymers, such as HPMC, HEC, PEO, and PAM, have been successfully used to separate these two fragments. However, the presence of intercalating dyes in the running buffer generally decreases the resolution of 434 bp and 458 bp.

For the first time, the present invention achieves total separation of 22 fragments in pBR322/Hae III. The problem encountered in previous attempts to separate the 22 fragments was the large difference in size between the small fragments and the large fragments. In order to detect the smallest 8 bp fragment, a relatively large amount of the large fragments has to be injected into the capillary, which may result in sample overloading and makes it difficult to achieve the necessary resolution if the detection is not sensitive enough. In the examples cited herein, a counting-mode photomultiplier tube ("PMT") was used for detection. The DNA sample used in Example 10 is described separately in Example 10.

Reagents

The reagents for the following examples were obtained from commercial sources. Acrylamide, ammonium persulfate, tris(hydroxymethyl)aminomethane (Tris), boric acid, ethylenediaminetetraacetic acid ("EDTA"), ethidium bromide and pBR322 Hae III digest were purchased from Sigma (St. Louis, Mo.). The pBR322/Msp I DNA was purchased from New England Biolabs (Beverly, Mass.). N, N, N',N'-tetramethylenediamine ("TEMED") was purchased from Fisher Scientific (Pittsburgh, Pa.). Poly (N-vinylpyrrolidone) ("PVP") with a molecular weight of 1,000,000 and polyacrylamide (PAM) with a molecular weight of 5,000,000–6,000,000 were purchased from Polysciences, Inc. (Warrington, Pa.). The electrophoresis buffer was 1×TBE (89 mM Tis/89 mM boric acid/2.5 mM EDTA) with 1 µg/ml ethidium bromide. The two DNA samples were diluted to 10 µg/ml with water before use. The reagents used in Example 10 are described separately in Example 10.

Laser-Induced Fluorescence Detection System

A laser-induced fluorescence detection system was used in the examples for capillary electrophoresis detection. The system included a water-cooled Ar ion laser which was used to generate an excitation beam with wavelength ($\lambda$) of 488 nm and an incident power of about 5 mW. The laser beam was focused by a lens with a 25-cm focal length, reflected by a dichroic mirror (550DRLP, Omega Optical, Brattleboro, Vt.), and focused again using a 10× objective to a spot within the separation channel. The fluorescence was collected by the objective, passed through the dichroic mirror, and filtered by a bandpass filter (605DF50, Omega Optical, Brattleboro, Vt.) to the photomultiplier tube ("PMT") (Hamamatsu R928, Hamamatsu Corporation, Bridgewater, N.J.). Images of the capillary were made using a charge coupled device (CCD) camera (SONY SSC-M350, SONY Corporation, New York, N.Y.). A white beam from the illuminator on the microscope illuminated the capillary. The image from the illuminated capillary was then focused by the objective, reflected by a slide in-and-out mirror, magnified by a Zoom 6000 System (D. O. Industries, Rochester, N.Y.) and then detected by the CCD camera. The microscope and the CCD camera (Karl Zeiss, Melville, N.Y.) provided good optical quality and fast alignment.

Example 1

For this example, 1-ml solutions with desired concentrations of PVP and acrylamide were prepared in 1×TBE and stored in a refrigerator overnight to ensure a homogeneous dissolution. The solutions were then purged for 30 minutes with high-purity nitrogen to minimize dissolved oxygen. Polymerization was initiated by the addition of 1 µl TEMED and 10 µl 10% w/v ammonium persulfate ("APS") and allowed to proceed to completion for several hours. Laser light scattering studies showed that this procedure allowed the polymerization of PAM with an average molecular weight of about 400,000 g/mol without significant variations at different concentrations of acrylamide and PVP. For the purpose of comparison, pure PAM solutions were also synthesized under the identical conditions. The pure PAM solutions had about the same average molecular weight of 400,000 g/mol.

Example 2

This example uses PAM and PVP to examine the combining of two different polymers to form an interpenetrating network. Due to the totally different chemical structures of PAM and PVP, interpenetrating networks cannot be prepared by dissolving PVP and PAM in 1×TBE buffer. Therefore, the compatibility of PAM and PVP was the first consideration in the preparation of a solution. Initially, PVP having a molecular weight of one million g/mol and PAM with a molecular weight of five million g/mol were dissolved in 1×TBE buffer. At PVP concentrations of 2%, 4% and 6% (all concentrations are w/v %), phase separation was observed when the PAM concentrations were 2%, 1% and 1%, respectively. Even for a solution mixture of PVP and PAM without phase separation, the DNA separation was still poor. The poor separation was attributed to micro-phase separation of the mixtures. To avoid this problem, PAM was synthesized in a PVP solution matrix so that the PAM chains were grown in a network of PVP chains. This produced more homogenous mixtures of PVP and PAM. Laser light scattering studies showed that interpenetrating networks of PVP and PAM were formed by this synthesis. These interpenetrating networks were found to provide efficient DNA separation.

Example 3

In this example, interpenetrating networks of PAM and PVP were used for separations of the 22 DNA fragments of pBR322/Hae III in the range of 8 to 587 bp. The separations were carried out in a 10/12 cm effective/total length capillary with a 100/365 µm ID/OD. The injection was performed at 50 V/cm for 3 seconds and the separation electric field strength was 100V/cm. The highest separation efficiency reached by the PAM/PVP networks had an order of $10^7$ theoretical plate numbers per meter, as shown in FIGS. 1 and 2. By comparison, a separation medium containing 4% (i.e., w/v %) PAM and no PVP had little sieving ability of DNA fragments. PVP was then added to the 4% PAM in accordance with the method of the present invention in concentrations of 0.5%, 1%, 2% and 4%. The interpenetrating networks with PAM and PVP greatly increased the separation ability. These results are shown in FIGS. 1A to 1D. The difference in the migration times for the four samples is believed to be caused by the different mesh sizes of the four separation media. By varying the ratio of PVP to PAM, the mesh size of the separation media can be controlled.

Example 4

Figure 2A:
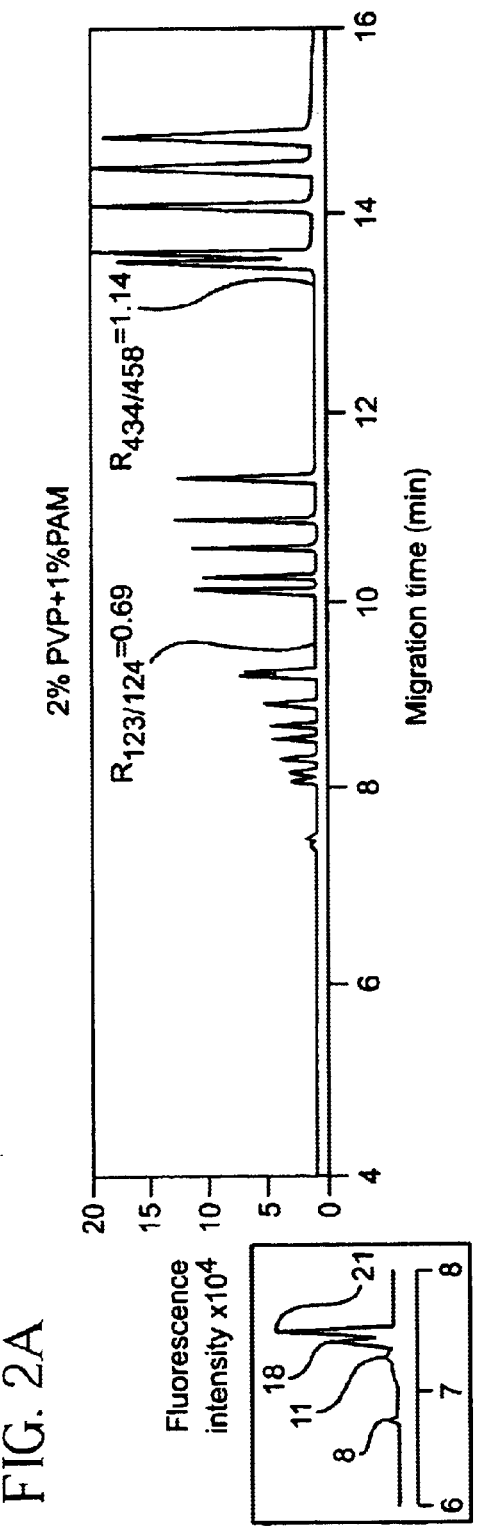
FIGS. 2A–2D show the test results for a separation of pBR 322/Hae III DNA by CE in interpenetrating networks of a fixed amount of PVP and varying amounts of PAM.
Figure 2B:
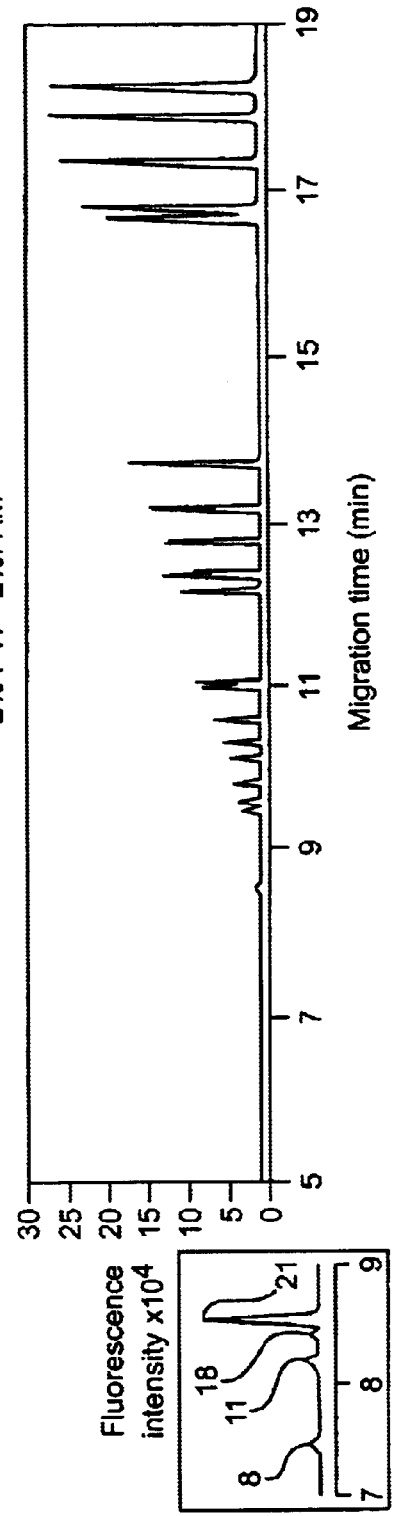
Figure 2C:
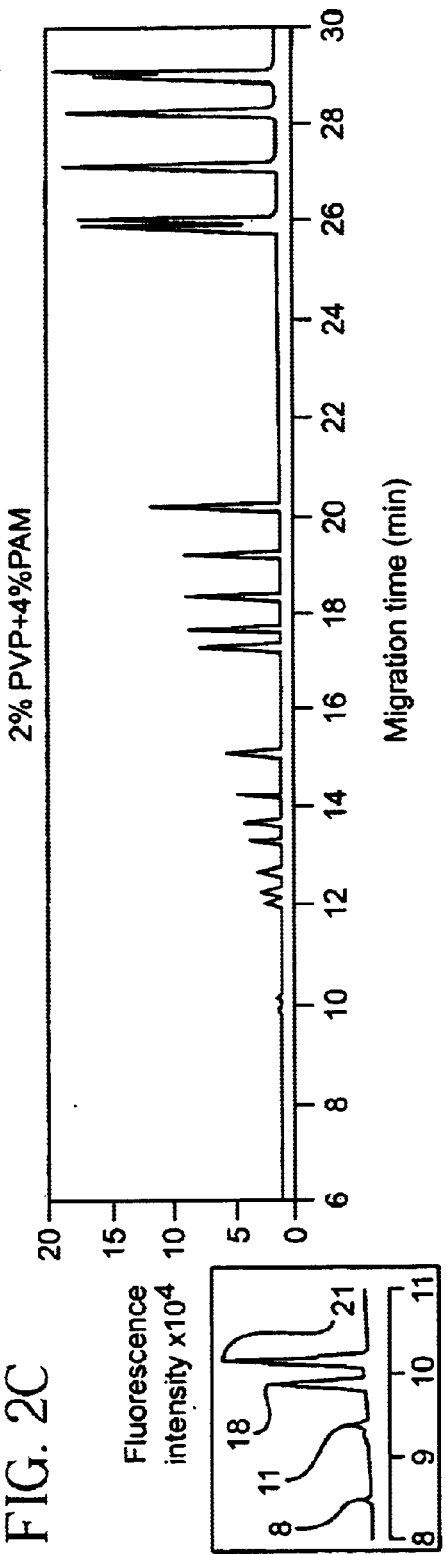
Figure 2D:
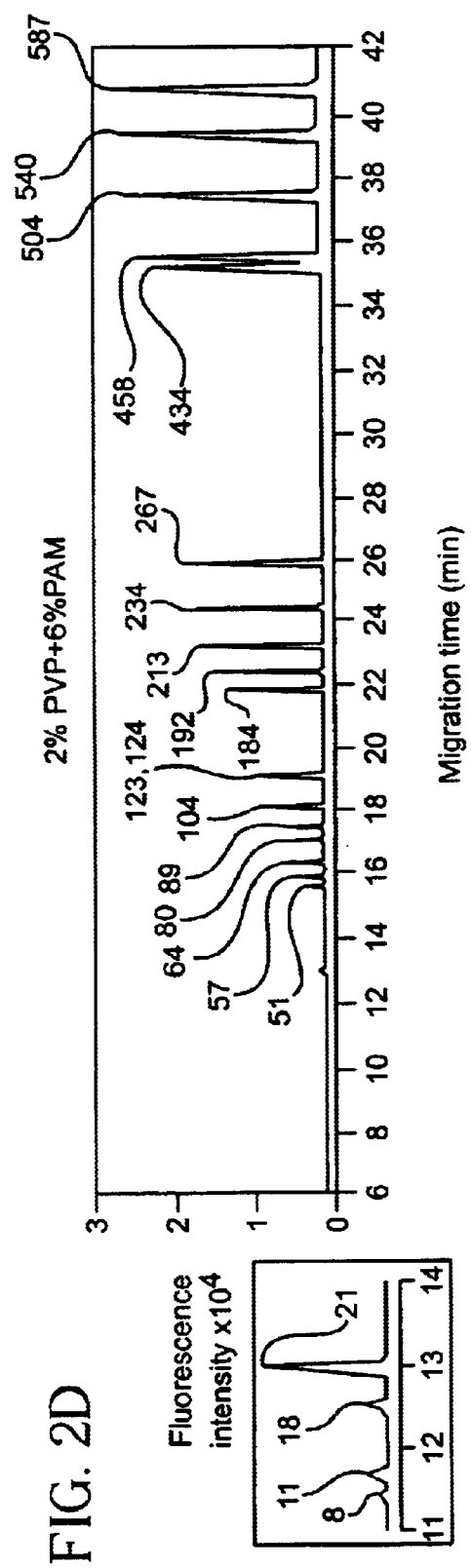
Figure 3:
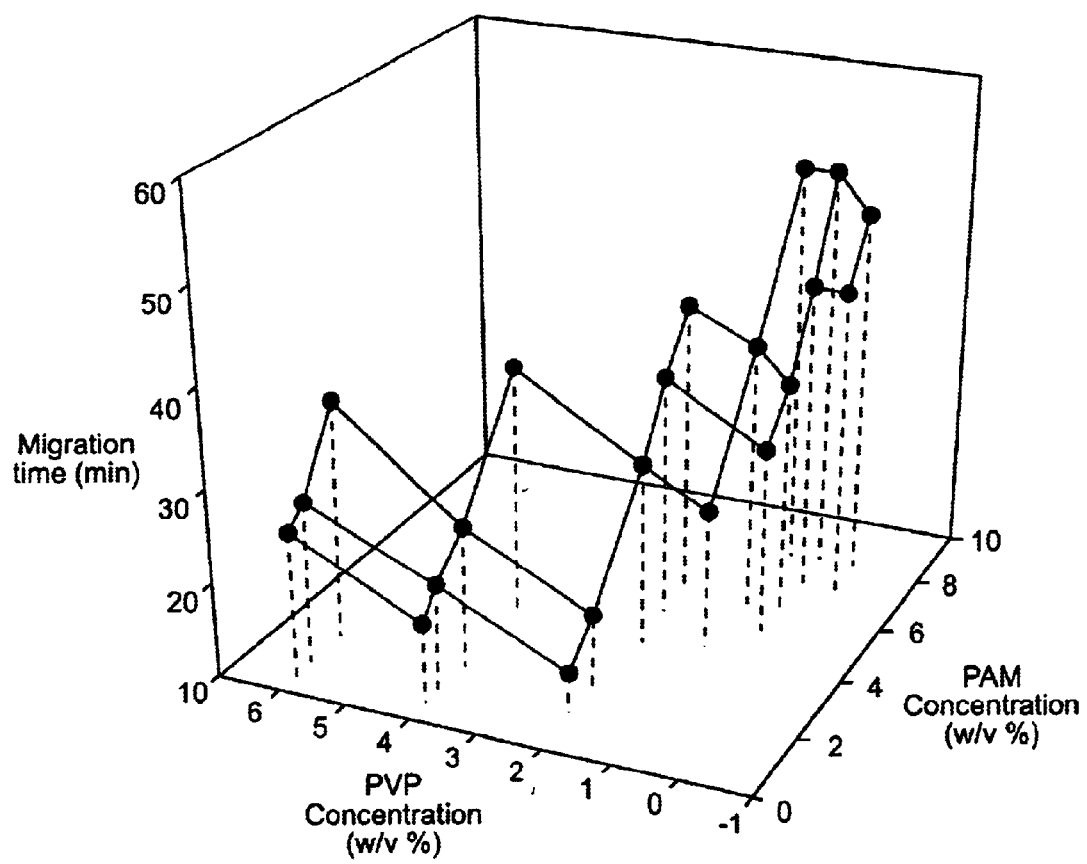
FIG. 3 shows the dependence of migration time of the 587 bp fragment for a separation of pBR 322/Hae III DNA by CE in interpenetrating networks of PAM and PVP.

This example demonstrates the effect of different concentrations of PVP in a PAM/PVP separation medium. For this example, the same DNA and separation conditions were used as in Example 3. A pure 2% (i.e., w/v %) PVP separation medium was tested and found to have little sieving ability of DNA fragments. Interpenetrating networks were then prepared from 2% PVP and PAM concentrations of 1%, 2%, 4%, 6%. These networks were used as separation media and FIGS. 2A to 2D show that the sieving ability of 2% PVP had been greatly increased by the addition of PAM. The separations as shown in FIG. 2A, with 2% PVP+1% PAM were significantly better and faster than similar separations using PAM alone. For example, under the same separation conditions, resolution similar to those shown in FIG. 2A could only be achieved by using at least a 6% PAM solution and with much longer run times. When pure PVP was used, the same separation as shown in FIG. 2A could not be achieved even at a PVP concentration of 15%. Further tests showed that a separation medium composition of 2% PVP and 1% PAM was the optimum combination for a fast separation of pBR322/HaeIII with good resolution of both 123/124 and 434/458 bp, as illustrated in FIG. 3. At a PVP concentration of 4%, a PAM concentration of 0.5% also provided good separation. However, the separation run time was somewhat longer than the 2% PVP/1% PAM solution and about the same as the 2% PVP+2% PAM solution mixture run time.

Example 5

This example demonstrates the effect of the inner diameter of the capillary on DNA separation. Interpenetrating networks of 2% (i.e., w/v %) PVP+1% PAM were used for separations of the 22 DNA fragments of pBR322/Hae III in the range of 8 to 587 bp. The separations were carried out in a 10/12 cm effective/total length capillary. The injections were performed at 50 V/cm for 3 seconds and the separation electric field strength was 100V/cm.

FIG. 2A shows the test results for a 100 µm ID capillary. The resolutions of 123/124 bp and 434/458 bp were calculated to be 0.69 and 1.14 using equation (1). It was found that these resolutions could be increased by decreasing the inner diameter of the capillary. FIG. 4B shows the results when the same 2% PVP+1% PAM interpenetrating network was used as a separation medium and the inner diameter of the capillary was decreased from 100 µm to 50 µm. The resolutions of 123/124 bp and 434/458 bp were calculated and found to have increased to 0.87 and 1.54.

Example 6

In this example, the effect of electric field strength was studied and it was found that the resolution could be improved further by varying the applied electric field. Interpenetrating networks of 2% (i.e., w/v %) PVP+1% PAM were used for separations of the 22 DNA fragments of pBR322/Hae III in the range of 8 to 587 bp and the results are shown in FIGS. 4A to 4D. The separations were carried out in a 10/12 cm effective/total length capillary with a 50 µm ID. The injections were performed at 50 V/cm for 3 seconds. The separation electric field strengths were: 50V/cm for the tests reported in FIG. 4A; 100V/cm for the tests reported in FIG. 4B; 200V/cm for the tests reported in FIG. 4C; and a gradient of from 200V/cm to 25V/cm with a duration time of 12 minutes and 25 V/cm thereafter for the tests reported in FIG. 4D.

Figure 4C:
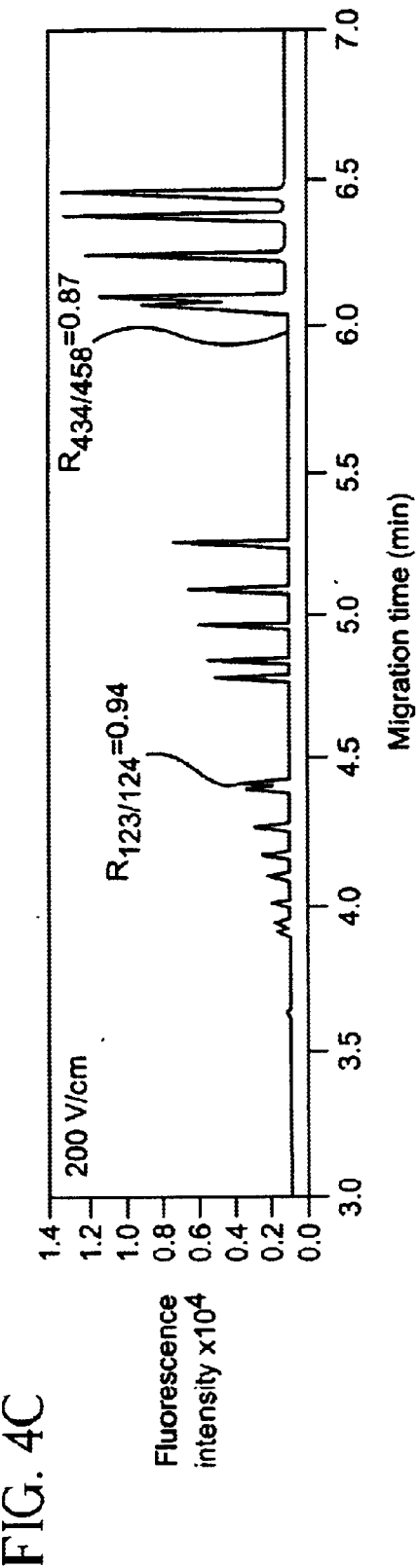
Figure 4D:
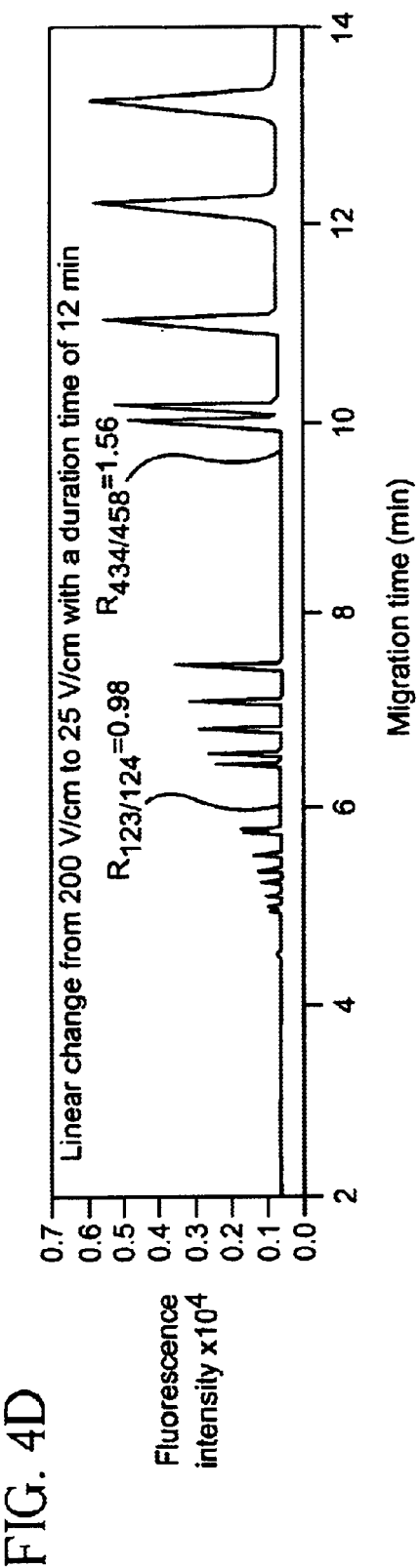

When the applied electric field strength was increased from 100 V/cm to 200 V/cm, the separation was completed within 6.5 min, as demonstrated in FIG. 4C. While the resolution of 123/124 bp was increased to 0.94, the resolution of 434/458 bp was decreased to 0.87. When the applied electric field strength was decreased from 100 V/cm to 50 V/cm, 30 minutes was required to complete the separation, as shown in FIG. 4A. The resolution of 123/124 bp was decreased to 0.67 and the resolution of 434/458 bp was increased to 1.72. In order to achieve a better resolution of both 123/124 bp and 434/458 bp in a single run, a gradient electric field strength that changed with time was tried. For a linear electric field gradient from 200 V/cm to 25 V/cm with a time duration of 12 min being used, the separation was completed within 14 minutes with a resolution of 0.98 and 1.56 for 123/124 bp and 434/458 bp, respectively, as shown in FIG. 4D.

FIG. 4C shows that the separation medium of the present invention, achieved a separation time of about 6.5-minutes using a capillary with an effective separation length of 10 cm and an electric field strength of 200 V/cm. When the sampling frequency increased, the peak became lower and the smaller peaks became practically invisible. The faster separations were mainly due to the use of low concentrations of the separation medium. In addition, the entangled networks of the present invention have lower molecular weights than mediums that were previously used to achieve equivalent separation results. The lower concentration allows the DNA fragments to pass through the medium more quickly and, therefore, provide faster run times.

Example 7

Figure 5:
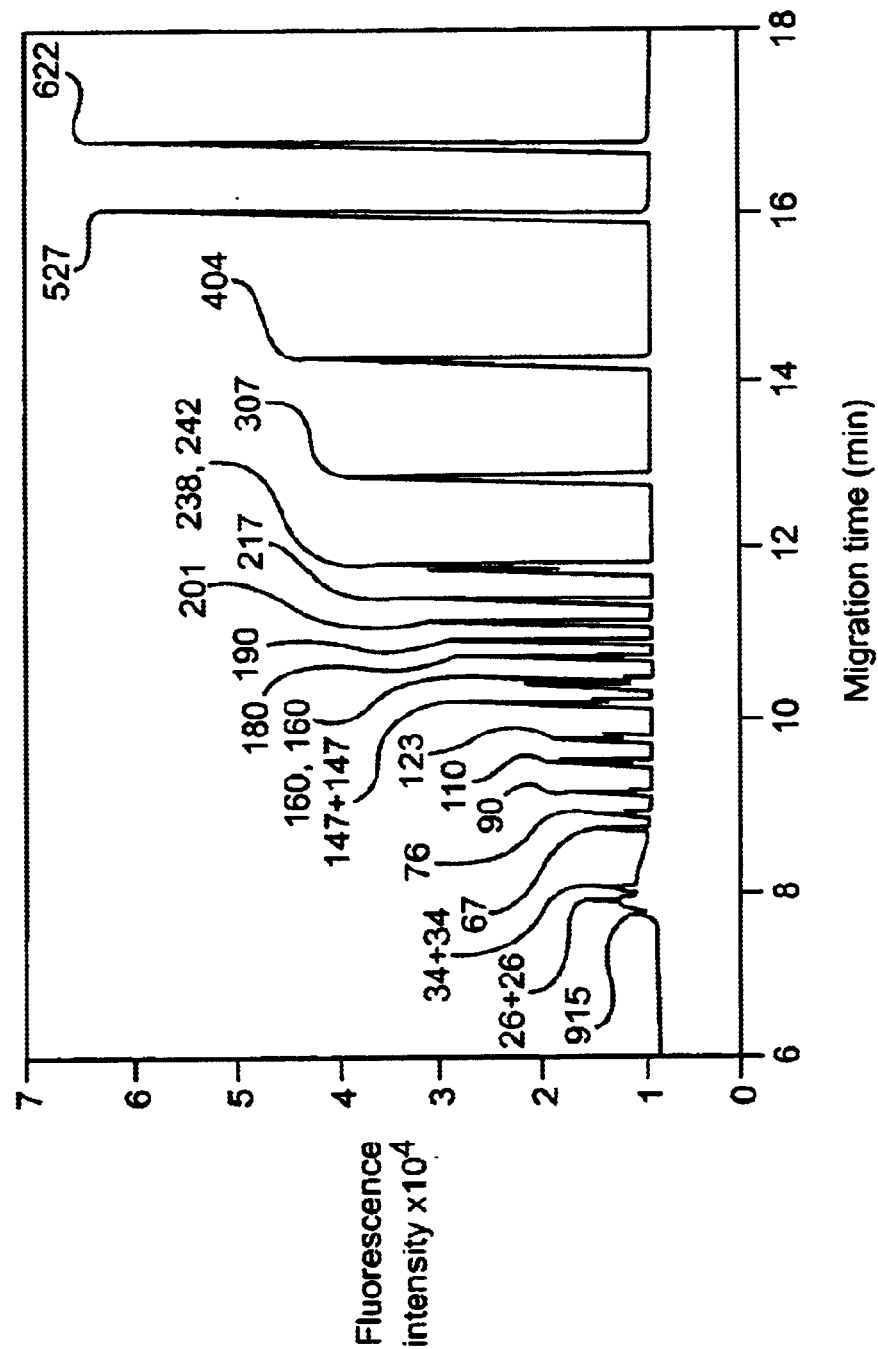
FIG. 5 shows the separation times of pBR 322/MSP I using a separation medium of 2% PVP+2% PAM.

In this example, the sieving ability of a 2% (i.e., w/v %) PVP+2% PAM matrix was demonstrated by the CE separation of pBR322/Msp I DNA. The separation was carried out in a 10/12 cm effective/total length capillary with a 100/365 μm ID/OD. The injection was performed at 50 V/cm for 3 seconds and the separation electric field strength was 100V/cm. This sample contained four pairs of fragments with the same lengths: 26, 34, 147 and 160 bps. Even though the separation was completed in only 17 min, the two 160 bp fragments were still successfully separated with a resolution of 1.24. The results are shown in FIG. 5.

Example 8

Figure 6A:
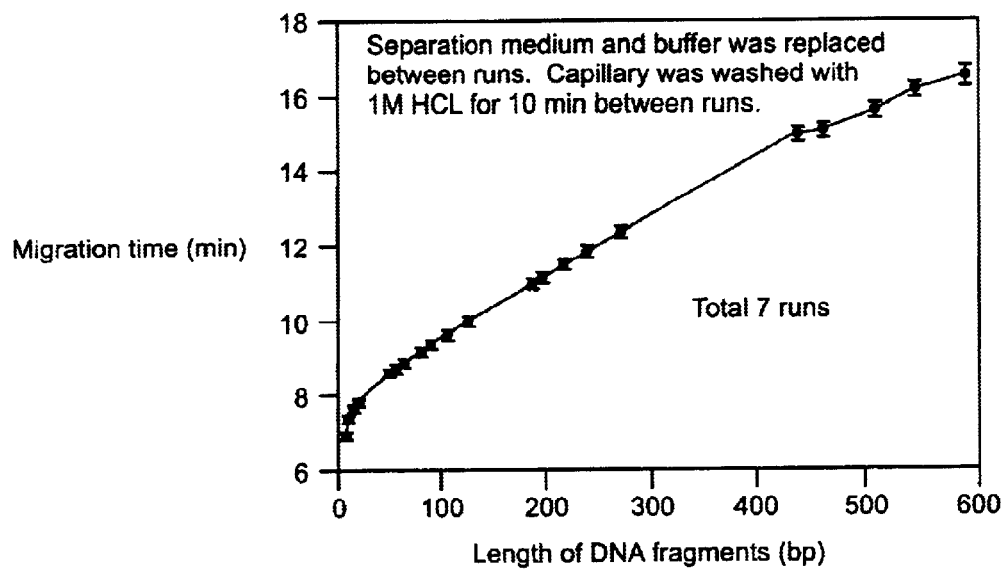
FIGS. 6A and 6B are graphs of migration time versus length of DNA fragments for multiple runs of the same separation medium.
Figure 6B:
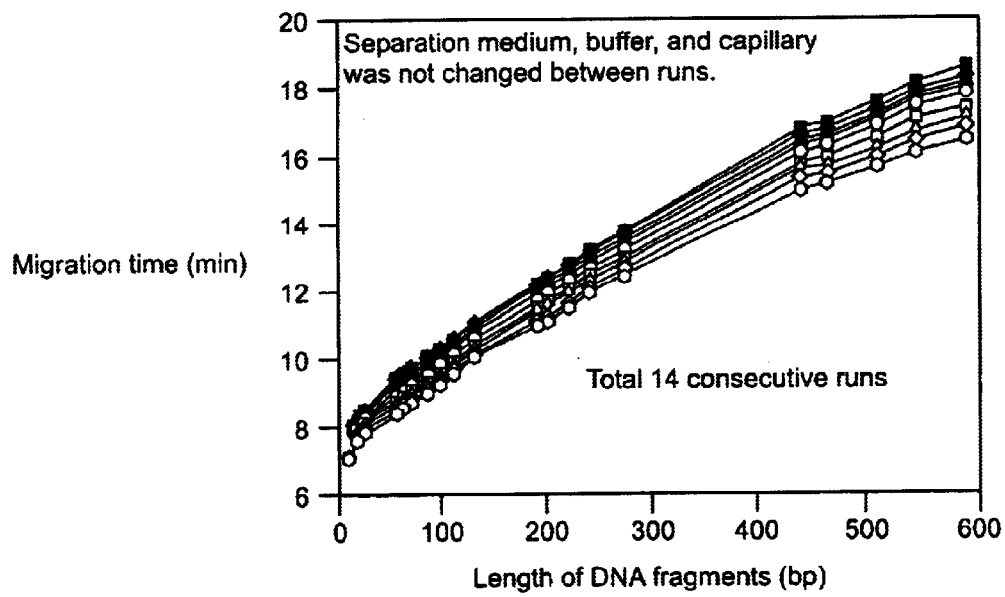
Figure 7A:
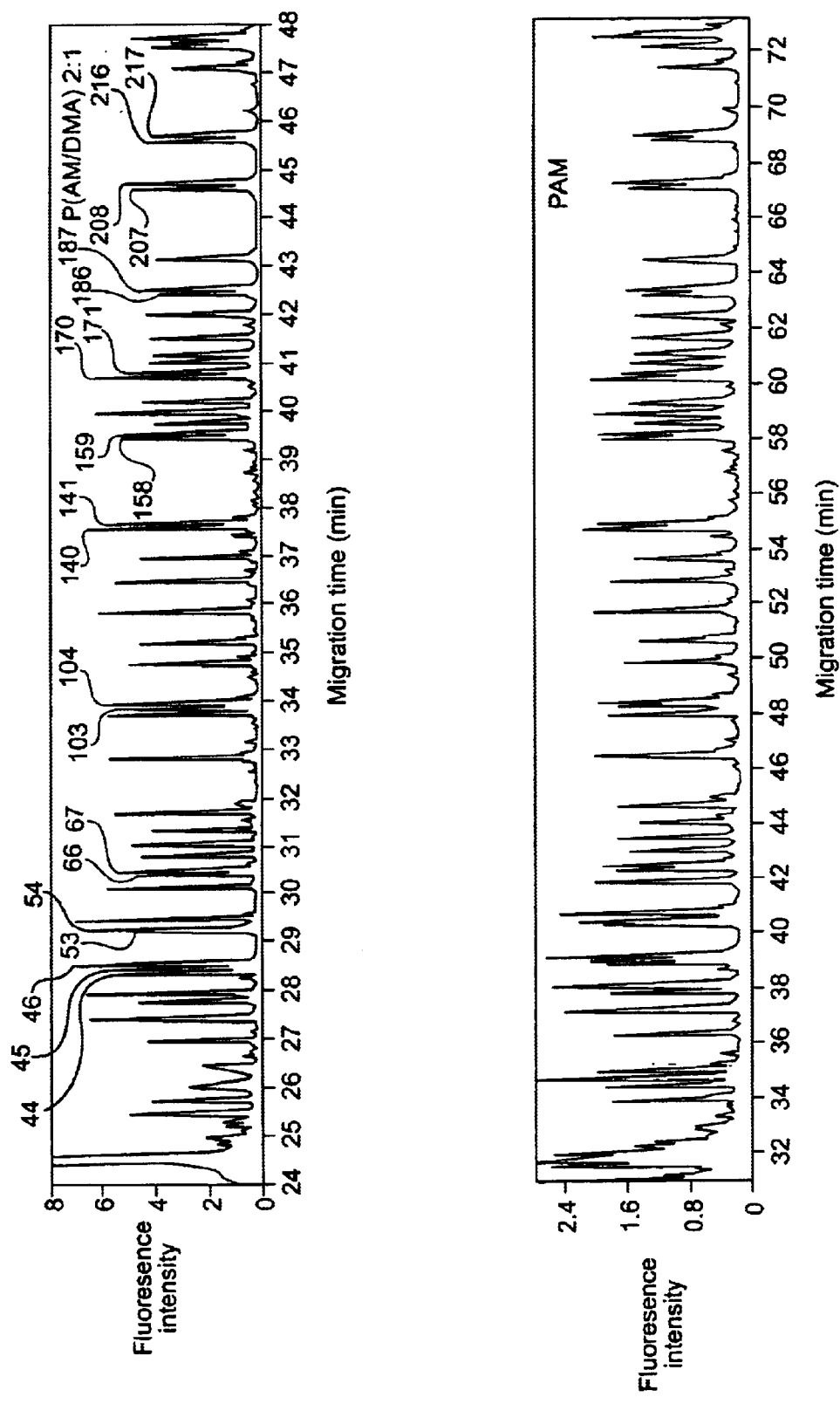
FIGS. 7A–&D show a comparison of the separation times for single-stranded DNA using P(AM/DMA) 2:1 and PAM.
Figure 7B:
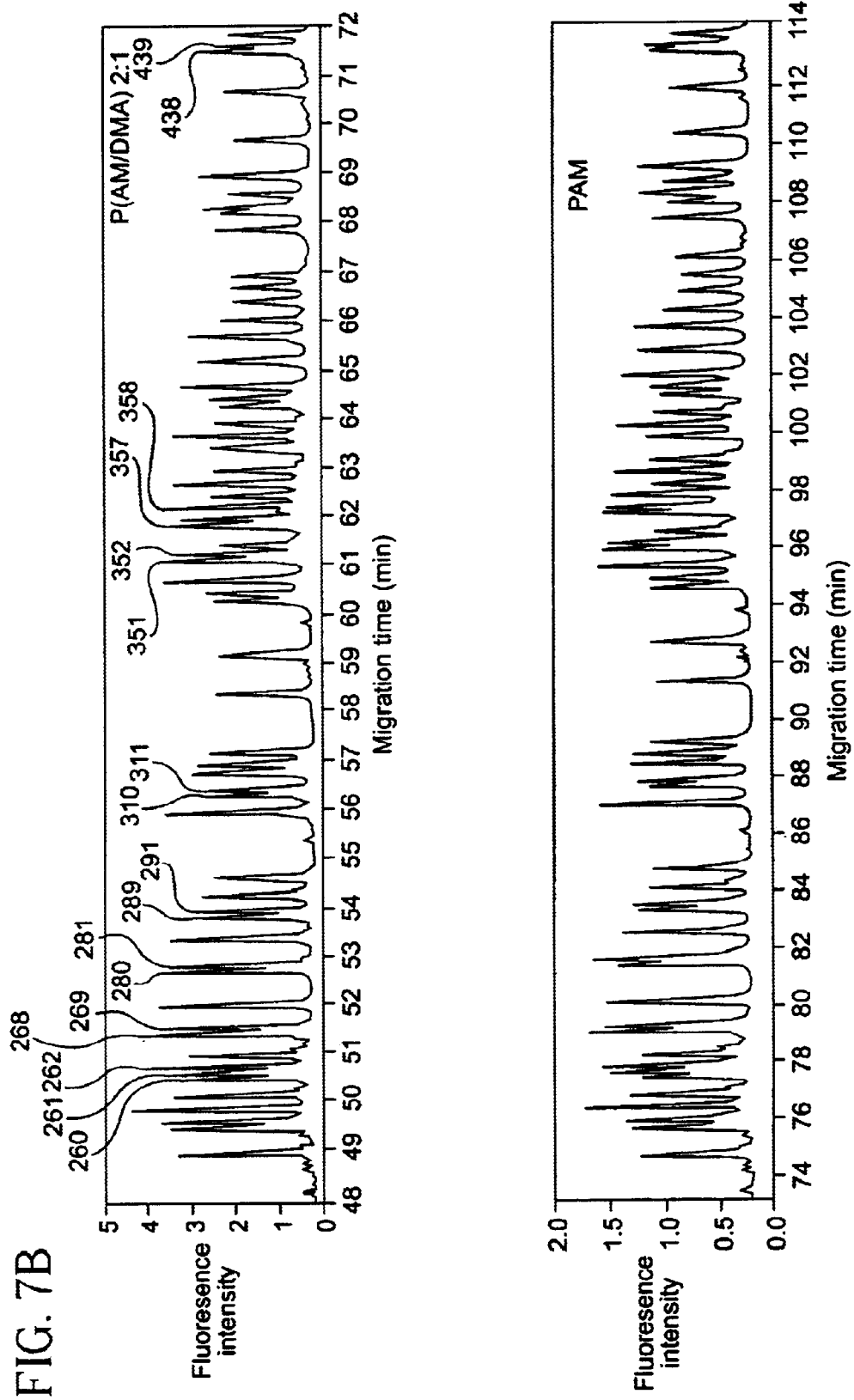
Figure 7C:
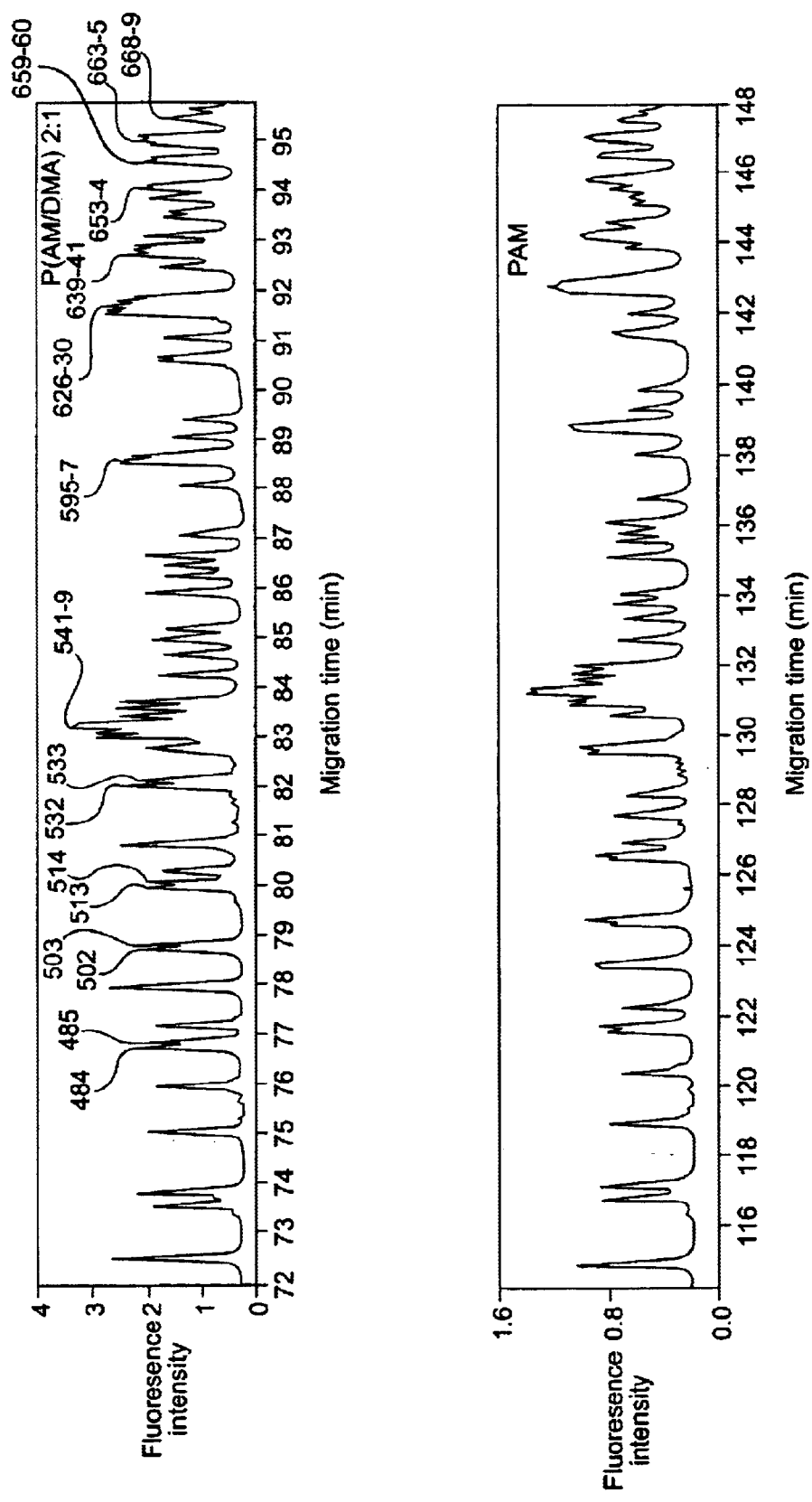
Figure 7D:
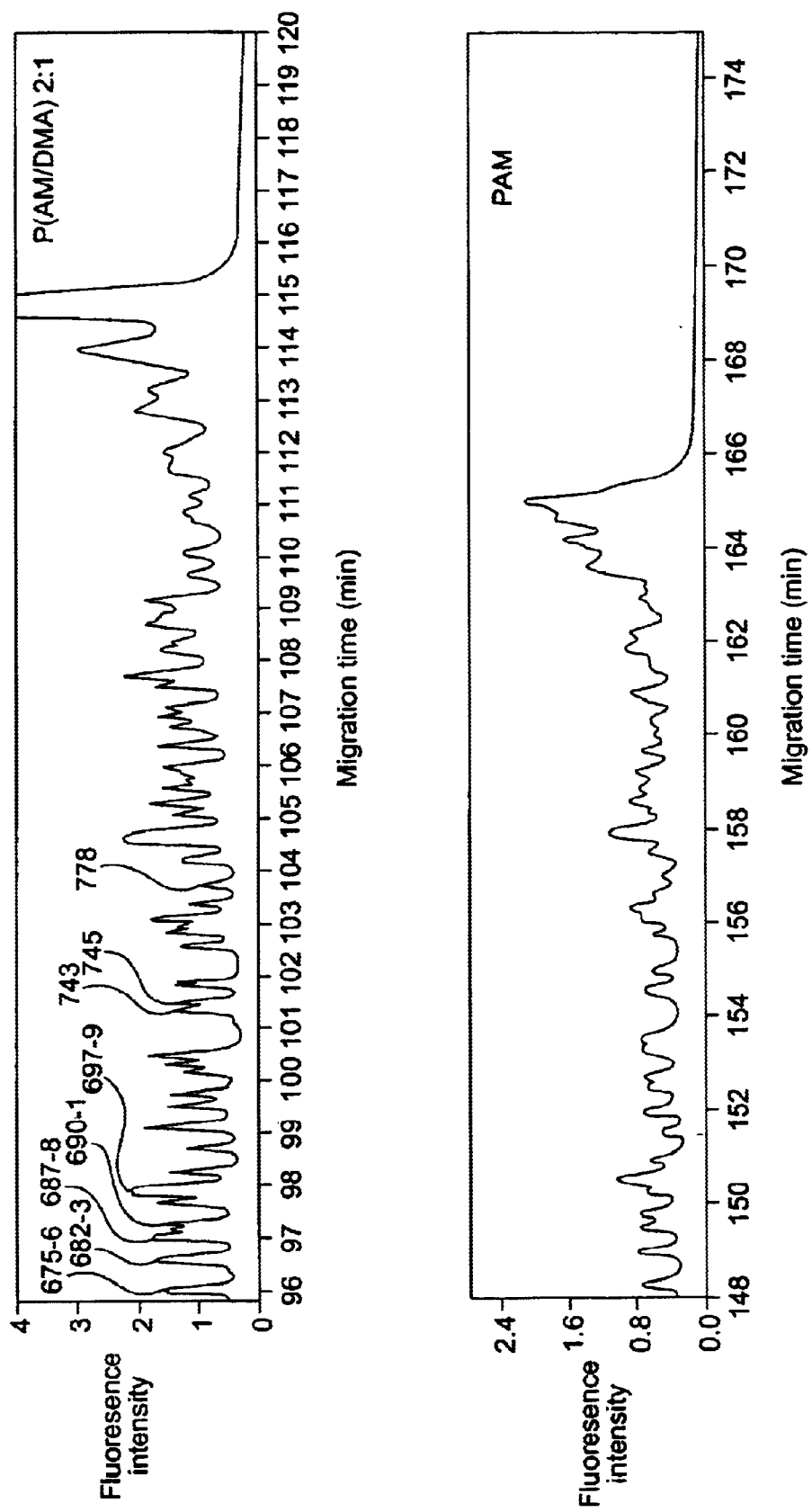

In this example, the separation reproducibility for the separation of pBR322/Hae III was investigated and the test results are shown in FIG. 6. For the test results shown in FIG. 6A, the separation medium and the separation buffer were replaced after each run and the capillary was washed with 1 N HCl for 10 minutes between runs. The relative standard deviation of the migration time measured for each DNA fragment was less than 1% (i.e., w/v %) in seven runs, suggesting that the coating of the capillary inner wall was quite reproducible. For the test results shown in FIG. 6B, the same capillary, buffer and separation medium of 2%PVP+ 2% PAM were used for each of the test runs. For the first seven runs, the relative standard deviation of the migration time was still less than 1.4%. After that, the migration time decreased. However, in the 14 consecutive runs, the separation of the pBR322/Hae III remained within acceptable limits.

Example 9

For this example, PAM and copolymers of acrylamide ("AM") and dimethylacrylamide ("DMA") were prepared. Monomers of AM (or AM and DMA) with a total concentration of 1.4 M were mixed with TEMED, resulting in a TEMED concentration of 0.09 μl/ml in the solution mixture. The solution mixture was then cooled in a 1° C. cold water bath and purged with ultra high purity helium for 5 hours to minimize dissolved oxygen. Polymerization was initiated by the addition of 50% ammonium persulfate ("APS") to a final APS concentration of 0.09 mg/ml and allowed to proceed to completion for 24 hours at 1° C. The solution was then diluted to 0.11 M (based on monomer concentration) and after shaking for three weeks, the solution was homogenous. Acetone was added to precipitate the polymer product in the solution. The polymer was then dried under vacuum. The copolymers of AM and DMA that were formed were characterized. An AM to DMA ratio of 2.94, 1.85 and 1.06 was determined by NMR. The molecular weight of the copolymers was estimated to be similar to that of PAM (with Mv of about $2.2 \times 10^6$ Da (or 2.2 mDa)).

Example 10

In this example, copolymers of AM and DMA with molar ratios of 3:1, 2:1, 1:1, respectively, as well as PAM were used to separate single-stranded DNA fragments.

The electrophoresis buffer for the separation of single-stranded DNA was 1×TTE (50 mM Tris/50 mM TAPS/2.0 mM EDTA) for the anode and 1×TTE/5M urea for the cathode. All separation media were prepared in 1×TTE/5M urea buffer. To prepare a separation medium, 1×TTE/5M urea was added to a known weight of dry PAM or the random copolymers P(AM/DMA) to the desired concentration. After the PAM or the random copolymer was swollen by the buffer overnight, the solution was vortexed for 30 seconds, twice a day with at least a 6 hour interval. After 2–3 days, the solution was degassed by ultracentrifugation ($7 \times 10^4$ g) before use.

Sequencing reactions were performed by using an ABI PRISM™ Dye Primer (−21 M13 forward) Cycle Sequencing Ready Reaction Kit with AmpliTaq® DNA Polymerase, FS (PE Biosystems/Perkin-Elmer Corp., Foster City, Calif.) on a pGEM3Zf(+) double-stranded template. Single dye-labeled sequencing reactions were performed using the FAM labeled primer and the C termination mix. The temperature cycling protocol was carried out using the GeneAmp PCR System 2400 (PE Biosystems/Perkin-Elmer Corp., Foster City, Calif.) with 15 cycles of 10 s at 95° C., 5 sec. at 50° C. and 1 min. at 70° C., followed by 15 cycles of 10 sec. at 95° C. and 1 min at 70° C. The reaction products were purified by ethanol precipitation and resuspended in 20 μl deionized formamide.

The separation of single-stranded DNA fragments with p(AM/DMA) 2:1 was compared with PAM under the same separation conditions: 50:40 cm total/effictive capillary length, 75 μm capillary inner diameter, 300 V/cm for 15 sec. injection and 150 V/cm for separation. When PAM was used, the inner wall of the capillary was covalently coated with PAM using the protocol described by Hjerten (*J. Chromatogr.*, 1985, 347, 191–198). When the copolymer was used, the capillary was simply washed with 1 M HCL for 10 minutes and the copolymer could coat the capillary dynamically, thereby avoiding the tedious covalent coating procedure. The results are shown in FIGS. 7A–D. It was found that (PAM/DMA) 2:1 provided better resolution for the single-stranded DNA fragments than PAM.

Figure 8A:
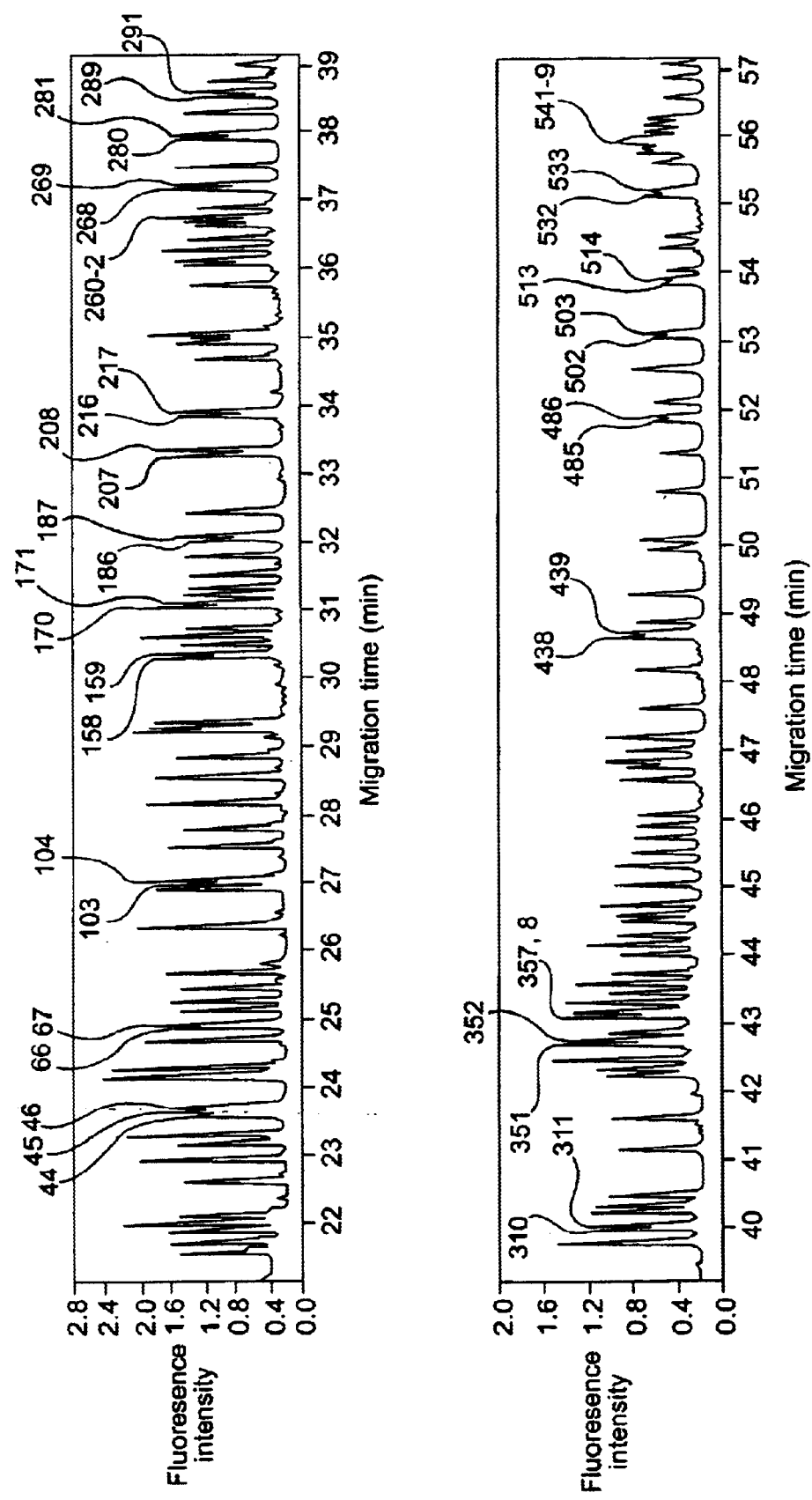
FIGS. 8A and 8B show the separation time under optimum conditions for single-stranded DNA using P(AM/DMA) 3:1.
Figure 8B:
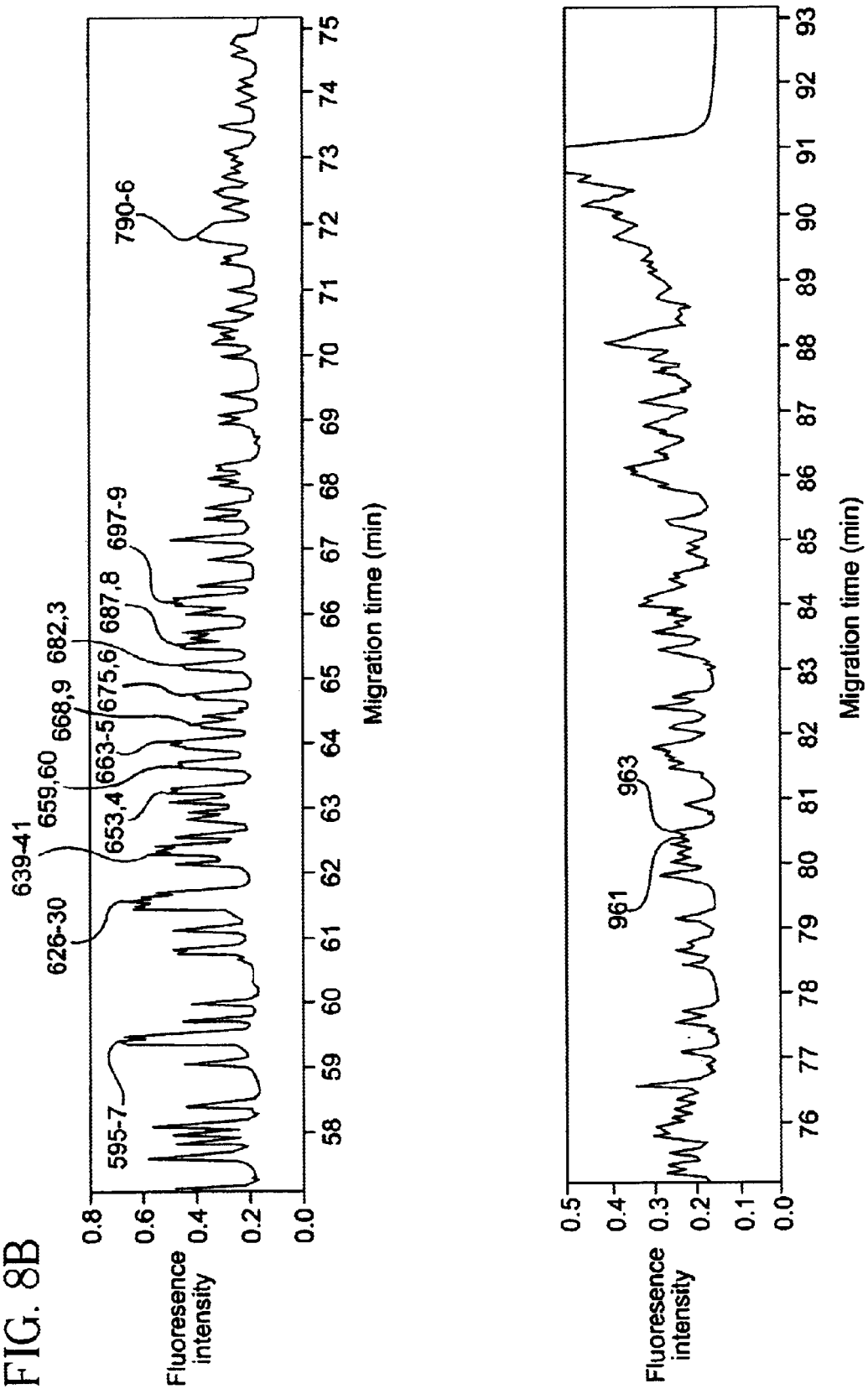

For the purpose of a fast separation with long read length, the separation conditions were further optimized to 2.5 w/v % copolymer concentration, 50/40 cm total/effective capillary length, 75 μm capillary inner diameter, 150 V/cm for 5 sec. injection, and 150 V/cm for separation. Under the optimized conditions, the use of P(AM/DMA) 3:1 has achieved the best results for the separtaion of single-stranded DNA fragments, which is shown in FIG. 8. A one base resolution of 0.55 and up to 699 bases and two base resolution of 0.61 up to 963 bases have been achieved without the aid of algorithms. It should be noted that the PAM and P(AM/DMA) had similar molecular weights. The performance of P(AM/DMA) could be further improved by using molecular weight copolymers and other random copolymers (slightly incompatible, one or both surface active) should have similar improvements when compared with the corresponding homopolymers.

Thus, while there have been described the preferred embodiments of the present invention, those skilled in the art will realize that other embodiments can be made without departing from the spirit of the invention, and it is intended to include all such further modifications and changes as come within the true scope of the claims set forth herein.

We claim:

1. A polymer solution for the efficient separation of charged macromolecules by electrophoresis comprising a plurality of polymers, wherein said polymers are different, do not phase separate when dissolved in solution and are entangled to form an interpenetrating network, wherein said interpenetrating network is prepared by synthesizing a first polymer in a matrix of a second polymer.

2. A polymer solution in accordance with claim 1, wherein said polymers are neutral and water-soluble.

3. A polymer solution in accordance with claim 1, wherein at least one of said polymers is polyacrylamide ("PAM"), N-substituted PAM, N,N-disubstituted PAM, modified polysaccharides, polyethylene oxide ("PEO"), polyvinylpyrrolidone ("PVP"), polyvinylalcohol ("PVA"), polyethylene glycol ("PEG"), or a random, a graft or a block copolymer based on the backbone monomer segments thereof, wherein nitrogen substitutes are selected from the group consisting of $C_1$ to $C_3$ alkyl, hydroxyl-substituted $C_1$ to $C_3$ alkyl, and methoxy-substituted $C_1$ to $C_3$ alkyl.

4. A polymer solution in accordance with claim 3, wherein said random, graft or block copolymer is EPE-type, N,N-dimethylacrylamide and N,N-diethylacrylamide ("P(DMA/DEA)"), a copolymer of poly(N-isopropylacrylamide) densely grafted with short poly(ethylene oxide) ("PNIPAM-g-PEO") or polyacrylamide-co-allyl-β-D-glucopyranoside ("P(AM/AG)").

5. A polymer solution in accordance with claim 3, wherein said polysaccharides are selected from the group consisting of liquified agrose, methylcellulose ("MC"), hydroxyethyl-cellulose ("HEC"), hydroxypropyl-methyl-cellulose ("HPMC"), hydroxypropylcellulose ("HPC"), glucomannan, galactonmannan and dextran.

6. A polymer solution in accordance with claim 1, wherein at least one of said polymers is a silica-absorbing polymer that suppresses electrophoendoosmotic flow and charged macromolecule-silica interactions.

7. A polymer solution in accordance with claim 6, wherein said silica-absorbing polymer is selected from the group consisting of PVP, PEO, EPE-type, N-substituted PAM and N,N-disubstituted PAM, and wherein nitrogen substitutes are selected from the group consisting of $C_1$ to $C_3$ alkyl, hydroxyl-substituted $C_1$ to $C_3$ alkyl, and methoxy-substituted $C_1$ to $C_3$ alkyl.

8. A polymer solution in accordance with claim 1, wherein said interpenetrating network has a more expanded structural formation than the entanglement structure of a corresponding homopolymer solution, and has a larger effective size than that of a corresponding homopolymer solution, representing an effective entanglement network greater than that of the corresponding homopolymers, and wherein said interpenetrating network has a lower molecular weight per volume than the corresponding homopolymers.

9. A polymer solution in accordance with claim 1, wherein said polymer solution provides at least a 500-base read length in one run for a single-stranded DNA separation.

* * * * *